US010059970B2

(12) United States Patent
Figge et al.

(10) Patent No.: US 10,059,970 B2
(45) **Date of Patent: *Aug. 28, 2018**

(54) MICROORGANISM FOR METHIONINE PRODUCTION WITH ENHANCED METHIONINE EFFLUX

(71) Applicant: EVONIK DEGUSSA GMBH, Essen (DE)

(72) Inventors: Rainer Figge, Le Crest (FR); Laurence Dumon-Seignovert, Pont du Chateau (FR)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/915,128

(22) PCT Filed: Sep. 1, 2014

(86) PCT No.: PCT/EP2014/068540
§ 371 (c)(1),
(2) Date: Feb. 26, 2016

(87) PCT Pub. No.: WO2015/028675
PCT Pub. Date: Mar. 5, 2015

(65) Prior Publication Data

US 2016/0177351 A1 Jun. 23, 2016

(30) Foreign Application Priority Data

Aug. 30, 2013 (EP) .................................... 13306189

(51) Int. Cl.

| | |
|---|---|
| ***C12P 13/12*** | (2006.01) |
| ***C12N 15/70*** | (2006.01) |
| ***C12N 1/00*** | (2006.01) |
| ***C12N 1/36*** | (2006.01) |

(52) U.S. Cl.
CPC ................ *C12P 13/12* (2013.01); *C12N 1/00* (2013.01); *C12N 1/36* (2013.01); *C12N 15/70* (2013.01)

(58) Field of Classification Search
None
See application file for complete search history.

(56) References Cited

FOREIGN PATENT DOCUMENTS

WO WO 2007/012078 A1 1/2007
WO WO 2008/082211 A1 7/2008
WO WO 2008/127240 A1 10/2008

OTHER PUBLICATIONS

Chica et al. Curr Opin Biotechnol. Aug. 2005;16(4):378-84.*
Singh et al. Curr Protein Pept Sci. 2017, 18, 1-11.*
Anderson, "Growth Requirements of Virus-Resistant Mutants of *Escherichia coli* Strain "B"," 1946, Bacteriology, Proc. N. A. S., vol. 32, pp. 120-128.
Carrier et al., "Library of Synthetic 5' Secondary Structures to Manipulate mRNA Stability in *Escherichia coli*," 1999 (Published on Web Jan. 9, 1999), Biotechnology Progress, vol. 15, No. 1, pp. 58-64 (8 pages).
Datsenko et al., "One-step Inactivation of Chromosomal Genes in *Escherichia coli* K-12 Using PCR Products," Jun. 6, 2000, PNAS, vol. 97, No. 12, pp. 6640-6645.
European Search Report, dated Jan. 13, 2014, for corresponding European Application No. 13 30 6189.
Heery et al., "Curing of a Plasmid from *E.coli* using High-voltage Electroporation," 1989, Nucleic Acids Research, vol. 17, No. 23, pp. 10131.
International Search Report (Form PCT/ISA/210), dated Dec. 1, 2014, for corresponding International Application No. PCT/EP2014/068540.
Jones et al., "Subunit Interactions in ABC Transporters: Towards a Functional Architecture," 1999, FEMS Microbiology Letters, vol. 179, pp. 187-202.
Kadner et al., "Energy Coupling for Methionine Transport in *Escherichia coli*," Sep. 1975, Journal of Bacteriology, vol. 123, No. 3, pp. 985-991.
Kadner, "Regulation of Methionine Transport Activity in *Escherichia coli*," Apr. 1975, Journal of Bacteriology, vol. 122, No. 1, pp. 110-119.
Kadner, "Transport Systems for L-Methionine in *Escherichia coli*," Jan. 1974, Journal of Bacteriology, vol. 117, No. 1, pp. 232-241.
Lerner et al., "Low Copy Number Plasmids for Regulated Low-level Expression of Cloned Genes in *Escherichia coli* with Blue/White Insert Screening Capability," 1990, Nucleic Acids Research, vol. 18, No. 15, pp. 4631.
Liebl et al., "Requirement of Chelating Compounds for the Growth of Corynebacterium glutamicum in Synthetic Media," 1989, Appl. Microbiol. Biotechnol., vol. 32, pp. 205-210.
Merlin et al., "The *Escherichia coli* metD Locus Encodes an ABC Transporter Which Includes Abc (MetN), YaeE (MetI), and YaeC (MetQ)," Oct. 2002, Journal of Bacteriology, vol. 184, No. 19, pp. 5513-5517.
Riedel et al., "Characterization of the Phosphoenolpyruvate Carboxykinase Gene from Corynebacterium glutamicum and Significance of the Enzyme for Growth and Amino Acid Production," 2001, J. Mol. Microbiol. Biotechnol., vol. 3, No. 4, pp. 573-583.

(Continued)

*Primary Examiner* — Christian Fronda
(74) *Attorney, Agent, or Firm* — Birch, Stewart, Kolasch & Birch, LLP

(57) ABSTRACT

The present invention is related to a recombinant *Escherichia coli* (*E. coli*) strain optimised for the fermentative production of methionine and/or its derivatives, wherein in said recombinant strain, the methionine import is attenuated and the methionine efflux is enhanced. It is also related to a method for optimising the fermentative production of methionine or its derivatives comprising the steps of: a. culturing a recombinant microorganism wherein in said microorganism, the methionine import is attenuated and the methionine efflux is enhanced, in an appropriate culture medium comprising a fermentable source of carbon and a source of sulphur, and b. recovering methionine and/or its derivatives from the culture medium.

6 Claims, No Drawings

Specification includes a Sequence Listing.

(56) References Cited

OTHER PUBLICATIONS

Saunderson, "Comparative Metabolism of L-methionine, DL-methionine and DL-2-hydroxy 4-methylthiobutanoic Acid by Broiler Chicks," 1985, British Journal of Nutrition, vol. 54, pp. 621-633.

Schaefer et al., "Automated Sampling Device for Monitoring Intracellular Metabolite Dynamics," 1999, Analytical Biochemistry, vol. 270, pp. 88-96.

Trötschel et al., "Characterization of Methionine Export in Corynebacterium glutamicum," Jun. 2005, Journal of Bacteriology, vol. 187, No. 11, pp. 3786-3794.

* cited by examiner

SEQUENCE LISTING

```
<160> NUMBER OF SEQ ID NOS: 30

<210> SEQ ID NO 1
<211> LENGTH: 245
<212> TYPE: PRT
<213> ORGANISM: Escherichia coli

<400> SEQUENCE: 1

Met Glu Ser Pro Thr Pro Gln Pro Ala Pro Gly Ser Ala Thr Phe Met
1               5                   10                  15
```

```
Glu Gly Cys Lys Asp Ser Leu Pro Ile Val Ile Ser Tyr Ile Pro Val
            20                  25                  30

Ala Phe Ala Phe Gly Leu Asn Ala Thr Arg Leu Gly Phe Ser Pro Leu
        35                  40                  45

Glu Ser Val Phe Phe Ser Cys Ile Ile Tyr Ala Gly Ala Ser Gln Phe
    50                  55                  60

Val Ile Thr Ala Met Leu Ala Ala Gly Ser Ser Leu Trp Ile Ala Ala
65                  70                  75                  80

Leu Thr Val Met Ala Met Asp Val Arg His Val Leu Tyr Gly Pro Ser
                85                  90                  95

Leu Arg Ser Arg Ile Ile Gln Arg Leu Gln Lys Ser Lys Thr Ala Leu
            100                 105                 110

Trp Ala Phe Gly Leu Thr Asp Glu Val Phe Ala Ala Ala Thr Ala Lys
        115                 120                 125

Leu Val Arg Asn Asn Arg Arg Trp Ser Glu Asn Trp Met Ile Gly Ile
    130                 135                 140

Ala Phe Ser Ser Trp Ser Ser Trp Val Phe Gly Thr Val Ile Gly Ala
145                 150                 155                 160

Phe Ser Gly Ser Gly Leu Leu Gln Gly Tyr Pro Ala Val Glu Ala Ala
                165                 170                 175

Leu Gly Phe Met Leu Pro Ala Leu Phe Met Ser Phe Leu Leu Ala Ser
            180                 185                 190

Phe Gln Arg Lys Gln Ser Leu Cys Val Thr Ala Ala Leu Val Gly Ala
        195                 200                 205

Leu Ala Gly Val Thr Leu Phe Ser Ile Pro Val Ala Ile Leu Ala Gly
    210                 215                 220

Ile Val Cys Gly Cys Leu Thr Ala Leu Ile Gln Ala Phe Trp Gln Gly
225                 230                 235                 240

Ala Pro Asp Glu Leu
                245


<210> SEQ ID NO 2
<211> LENGTH: 111
<212> TYPE: PRT
<213> ORGANISM: Escherichia coli

<400> SEQUENCE: 2

Met Ser Tyr Glu Val Leu Leu Leu Gly Leu Leu Val Gly Val Ala Asn
1               5                   10                  15

Tyr Cys Phe Arg Tyr Leu Pro Leu Arg Leu Arg Val Gly Asn Ala Arg
            20                  25                  30

Pro Thr Lys Arg Gly Ala Val Gly Ile Leu Leu Asp Thr Ile Gly Ile
        35                  40                  45

Ala Ser Ile Cys Ala Leu Leu Val Val Ser Thr Ala Pro Glu Val Met
    50                  55                  60

His Asp Thr Arg Arg Phe Val Pro Thr Leu Val Gly Phe Ala Val Leu
65                  70                  75                  80

Gly Ala Ser Phe Tyr Lys Thr Arg Ser Ile Ile Ile Pro Thr Leu Leu
                85                  90                  95

Ser Ala Leu Ala Tyr Gly Leu Ala Trp Lys Val Met Ala Ile Ile
            100                 105                 110


<210> SEQ ID NO 3
<211> LENGTH: 244
<212> TYPE: PRT
```

-continued

<213> ORGANISM: Citrobacter koseri

<400> SEQUENCE: 3

```
Met Glu Ser Pro Ala Pro Gln Ser Glu Pro Arg Pro Ala Thr Leu Thr
1               5                   10                  15

Glu Gly Phe Lys Asp Ser Leu Pro Ile Val Ile Ser Tyr Ile Pro Val
            20                  25                  30

Ala Phe Ala Phe Gly Leu Asn Ala Thr Arg Leu Gly Phe Thr Pro Leu
        35                  40                  45

Glu Ser Val Phe Phe Ser Cys Ile Ile Tyr Ala Gly Ala Ser Gln Phe
    50                  55                  60

Val Ile Thr Thr Met Leu Ala Ala Gly Ser Thr Leu Trp Val Ala Ala
65                  70                  75                  80

Leu Thr Val Met Ala Met Asp Val Arg His Val Leu Tyr Gly Pro Ser
                85                  90                  95

Leu Arg Ser Arg Ile Ser Gln Arg Leu Ser Lys Pro Lys Thr Ala Leu
            100                 105                 110

Trp Ala Phe Gly Leu Thr Asp Glu Val Phe Ala Ala Ala Thr Ala Lys
        115                 120                 125

Leu Val Arg Asp Asn Arg Arg Trp Ser Glu Trp Met Ile Gly Ile Ala
    130                 135                 140

Phe Cys Ser Trp Ala Ser Trp Val Leu Gly Thr Val Ile Gly Ala Phe
145                 150                 155                 160

Ser Gly Ser Gly Leu Leu Lys Gly Phe Pro Ala Val Glu Ala Ala Leu
                165                 170                 175

Gly Phe Met Leu Pro Ala Leu Phe Met Ser Phe Leu Leu Ala Ser Phe
            180                 185                 190

Gln Arg Lys Gln Thr Leu Cys Val Thr Ala Ala Leu Ile Gly Ala Leu
        195                 200                 205

Ala Gly Val Thr Leu Phe Ser Ile Pro Ala Ala Ile Leu Ala Gly Ile
    210                 215                 220

Ala Ser Gly Cys Leu Thr Ala Leu Ile Gln Ser Phe Trp Gln Gly Ala
225                 230                 235                 240

Pro Asp Glu Leu
```

<210> SEQ ID NO 4
<211> LENGTH: 111
<212> TYPE: PRT
<213> ORGANISM: Citrobacter koseri

<400> SEQUENCE: 4

```
Met Ser Tyr Glu Val Leu Leu Leu Gly Leu Leu Val Gly Cys Ala Asn
1               5                   10                  15

Tyr Cys Phe Arg Tyr Leu Pro Leu Arg Leu Arg Met Gly Asn Thr Arg
            20                  25                  30

Pro Ala Arg Arg Gly Ala Thr Gly Val Leu Leu Asp Thr Ile Gly Ile
        35                  40                  45

Ala Ser Ile Cys Ala Leu Leu Val Val Ser Thr Ala Pro Glu Val Met
    50                  55                  60

His Asp Ala Ser Arg Phe Ile Pro Thr Leu Val Gly Phe Ala Val Leu
65                  70                  75                  80

Gly Val Ser Phe Tyr Lys Thr Arg Ser Ile Ile Ile Pro Thr Leu Leu
                85                  90                  95

Ser Ala Leu Gly Tyr Gly Leu Ala Trp Lys Ile Glu Val Ile Leu
            100                 105                 110
```

<210> SEQ ID NO 5
<211> LENGTH: 245
<212> TYPE: PRT
<213> ORGANISM: Shigella flexneri

<400> SEQUENCE: 5

```
Met Glu Ser Pro Val Pro Gln Ser Glu Ser Arg Ser Ala Thr Leu Thr
1               5                   10                  15

Glu Gly Phe Lys Asp Ser Leu Pro Ile Val Ile Ser Tyr Ile Pro Val
            20                  25                  30

Ala Phe Ala Phe Gly Met Asn Ala Thr Arg Leu Gly Phe Thr Pro Val
        35                  40                  45

Glu Ser Val Phe Phe Ser Cys Ile Ile Tyr Ala Gly Ala Ser Gln Phe
    50                  55                  60

Val Ile Thr Thr Met Leu Ala Ala Gly Ser Ser Leu Trp Val Ala Ala
65                  70                  75                  80

Leu Thr Val Met Ala Met Asp Val Arg His Val Leu Tyr Gly Pro Ser
                85                  90                  95

Leu Arg Ser Arg Ile Ala Arg Gln Leu Ser Lys Pro Lys Ser Ala Leu
            100                 105                 110

Trp Ala Phe Gly Leu Thr Asp Glu Val Phe Ala Ala Ala Thr Ala Lys
        115                 120                 125

Leu Val Arg Asp Asn Arg Arg Trp Ser Glu Asn Trp Met Ile Gly Ile
    130                 135                 140

Ala Leu Cys Ser Trp Ala Ser Trp Val Leu Gly Thr Val Ile Gly Ala
145                 150                 155                 160

Phe Ser Gly Thr Gly Leu Leu Lys Gly Phe Pro Ala Val Glu Ala Ala
                165                 170                 175

Leu Gly Phe Met Leu Pro Ala Leu Phe Met Ser Phe Leu Leu Ala Ser
            180                 185                 190

Phe Gln Arg Asn Gln Thr Leu Cys Val Thr Ala Ala Leu Ala Gly Ala
        195                 200                 205

Leu Ala Gly Val Thr Leu Phe Ser Ile Pro Ala Ala Ile Leu Ala Gly
    210                 215                 220

Ile Val Cys Gly Cys Leu Thr Ala Leu Ile Gln Ser Phe Trp Gln Gly
225                 230                 235                 240

Gly Pro Asp Glu Leu
                245
```

<210> SEQ ID NO 6
<211> LENGTH: 111
<212> TYPE: PRT
<213> ORGANISM: Shigella flexneri

<400> SEQUENCE: 6

```
Met Ser Tyr Glu Val Leu Leu Leu Gly Leu Leu Val Gly Cys Val Asn
1               5                   10                  15

Tyr Cys Phe Arg Tyr Leu Pro Leu Arg Leu Arg Met Gly Asn Val Arg
            20                  25                  30

Pro Thr Lys Arg Gly Ala Thr Gly Ile Leu Leu Asp Thr Ile Gly Ile
        35                  40                  45

Ala Ser Ile Cys Ala Leu Leu Val Val Ser Thr Ala Pro Glu Val Met
    50                  55                  60

His Asp Ala Arg Arg Phe Val Pro Thr Leu Val Gly Phe Val Val Leu
65                  70                  75                  80
```

Gly Ala Ser Phe Tyr Lys Thr Arg Ser Ile Ile Ile Pro Thr Leu Leu
85 90 95

Ser Ala Leu Gly Tyr Gly Leu Ala Trp Lys Met Leu Phe Val Leu
100 105 110

<210> SEQ ID NO 7
<211> LENGTH: 242
<212> TYPE: PRT
<213> ORGANISM: Raoultella ornithinolytica

<400> SEQUENCE: 7

Met Glu Lys Pro Ala Pro Ala Ser Glu Ala Thr Leu Pro Glu Gly Ile
1 5 10 15

Lys Asp Ser Leu Pro Ile Val Ile Ser Tyr Ile Pro Val Ala Phe Ala
20 25 30

Phe Gly Leu Asn Ala Thr Arg Leu Gly Phe Thr Pro Leu Glu Ser Leu
35 40 45

Phe Phe Ser Cys Ile Ile Tyr Ala Gly Ala Ser Gln Phe Val Ile Thr
50 55 60

Ala Met Leu Ala Ala Gly Ser Ser Leu Trp Val Ala Ala Leu Thr Val
65 70 75 80

Met Ala Met Asp Val Arg His Val Leu Tyr Gly Pro Ser Leu Arg Ser
85 90 95

Arg Ile His Arg Ala Leu Asp Lys Arg Lys Thr Ala Leu Trp Ala Phe
100 105 110

Gly Leu Thr Asp Glu Val Phe Ala Ala Ala Thr Ala Lys Leu Val Arg
115 120 125

Asp Asn Arg Arg Trp Ser Glu Ser Trp Met Leu Gly Ile Ala Phe Thr
130 135 140

Ser Trp Ile Ser Trp Val Phe Gly Thr Leu Ile Gly Ala Tyr Ser Gly
145 150 155 160

Ser Gly Leu Leu Val Gly Phe Pro Ala Val Glu Ala Ala Leu Ser Phe
165 170 175

Met Leu Pro Ala Leu Phe Met Ser Phe Leu Leu Ala Ser Phe Gln Arg
180 185 190

Lys Gln Ser Leu Ser Val Thr Ala Ala Leu Ala Gly Ala Leu Gly Gly
195 200 205

Ile Ile Leu Phe Ser Ile Pro Ala Ala Ile Leu Ala Gly Ile Val Cys
210 215 220

Gly Cys Leu Ala Ala Leu Ile Gln Ala Ser Ile Gln Gly Met Pro Asp
225 230 235 240

Glu Gln

<210> SEQ ID NO 8
<211> LENGTH: 113
<212> TYPE: PRT
<213> ORGANISM: Raoultella ornithinolytica

<400> SEQUENCE: 8

Met Asn Asn Asn Val Leu Ile Ile Gly Ile Val Val Gly Cys Val Asn
1 5 10 15

Tyr Leu Phe Arg Tyr Leu Pro Leu Arg Leu Arg Ala Gly Asn Ala Arg
20 25 30

Pro Thr Arg Arg Gly Pro Leu Ser Val Leu Leu Asp Thr Ile Gly Ile
35 40 45

-continued

```
Ala Ser Ile Cys Ala Leu Leu Ile Val Ser Ser Val Pro Glu Ile Leu
    50                  55                  60

Ser Asp Ser Arg Arg Leu Leu Pro Thr Leu Val Gly Phe Thr Val Leu
65                  70                  75                  80

Gly Leu Ala Phe Trp Lys Thr Arg Ser Ile Ile Met Pro Thr Leu Leu
                85                  90                  95

Ser Ala Leu Ala Tyr Gly Ile Ala Trp Lys Ile Thr Thr Phe Leu Tyr
            100                 105                 110

Phe


<210> SEQ ID NO 9
<211> LENGTH: 250
<212> TYPE: PRT
<213> ORGANISM: Enterobacter sp. (R4-368)

<400> SEQUENCE: 9

Met Asp Met Asp Ser Ser Val Thr Ala Thr Lys Ser Thr Ser Asp Gln
1               5                   10                  15

Ser Ala Thr Phe Leu Glu Gly Ile Lys Asp Ser Leu Pro Ile Val Leu
            20                  25                  30

Ser Tyr Val Pro Val Ala Phe Ala Phe Gly Met Asn Ala Thr Lys Leu
        35                  40                  45

Gly Phe Thr Pro Leu Glu Ser Val Phe Phe Ser Cys Ile Ile Tyr Ala
    50                  55                  60

Gly Ala Ser Gln Phe Val Ile Thr Thr Met Leu Ala Ala Gly Ser Ala
65                  70                  75                  80

Leu Trp Val Ala Ala Leu Thr Val Met Ala Met Asp Val Arg His Val
                85                  90                  95

Leu Tyr Gly Pro Ser Leu Arg Ser Arg Ile Leu Gln Pro Leu Lys Asn
            100                 105                 110

Arg Lys Thr Ala Val Trp Ala Phe Gly Leu Thr Asp Glu Val Phe Ala
        115                 120                 125

Ala Ala Thr Ala Lys Leu Val Arg Asp Asn Arg Arg Trp Ser Glu Asn
    130                 135                 140

Trp Met Ile Gly Ile Ala Leu Phe Ser Trp Leu Ser Trp Val Ala Gly
145                 150                 155                 160

Thr Val Leu Gly Ala Phe Ser Gly Asp Gly Leu Leu Asp Gly Tyr Pro
                165                 170                 175

Ala Val Glu Ser Ala Leu Gly Phe Met Leu Pro Ala Leu Phe Met Ser
            180                 185                 190

Phe Leu Leu Ala Ser Phe Gln Arg Arg Gln Ile Ser Ala Val Thr Ala
        195                 200                 205

Ala Leu Leu Gly Ala Leu Ala Gly Val Thr Leu Phe Ser Ile Pro Ala
    210                 215                 220

Ala Ile Leu Ala Gly Ile Phe Ala Gly Cys Leu Ala Ala Leu Val Gln
225                 230                 235                 240

Ala Phe Tyr Gln Gly Ala Ser Asp Ala Gln
                245                 250


<210> SEQ ID NO 10
<211> LENGTH: 111
<212> TYPE: PRT
<213> ORGANISM: Enterobacter sp. (R4-368)

<400> SEQUENCE: 10

Met Arg Asn Glu Val Leu Leu Leu Gly Leu Leu Val Gly Cys Val Asn
```

-continued

```
1               5                   10                  15

Phe Leu Phe Arg Tyr Leu Pro Leu Arg Ile Arg Ala Gly Gln Ser Arg
            20                  25                  30

Pro Ala Lys Arg Gly Val Ser Gly Val Phe Leu Asp Thr Ile Gly Ile
        35                  40                  45

Ala Ser Ile Cys Ala Leu Leu Val Val Ser Cys Val Pro Glu Ile Ala
    50                  55                  60

Ala Asp Ser Arg Arg Leu Leu Pro Thr Leu Ala Gly Phe Ala Val Leu
65                  70                  75                  80

Gly Val Ser Phe Trp Lys Thr Arg Ser Ile Ile Leu Pro Thr Leu Leu
                85                  90                  95

Ser Ala Phe Ala Tyr Gly Ile Val Trp Lys Leu Leu Ala Asp Ala
            100                 105                 110


<210> SEQ ID NO 11
<211> LENGTH: 257
<212> TYPE: PRT
<213> ORGANISM: Yersinia enterocolitica subsp. enterocolitica

<400> SEQUENCE: 11

Met Gln Ser Gln Thr Thr Asp Ser Pro Ser Thr Ala Gln Pro Thr Ala
1               5                   10                  15

Thr Phe Ile Glu Gly Ile Thr Asp Ser Leu Pro Ile Val Ile Gly Tyr
            20                  25                  30

Leu Pro Val Ala Phe Ala Phe Gly Leu Ser Ser Val Lys Leu Gly Phe
        35                  40                  45

Thr Pro Trp Glu Ala Ile Phe Phe Ser Cys Ile Ile Tyr Ala Gly Ala
    50                  55                  60

Ser Gln Phe Val Ile Thr Ala Leu Leu Ser Ala Gly Met Ser Leu Trp
65                  70                  75                  80

Val Ser Ala Leu Thr Val Met Ala Met Asp Val Arg His Ile Leu Tyr
                85                  90                  95

Gly Pro Ala Leu Lys His Arg Ile Val Thr Arg Leu Ser Gly Lys Lys
            100                 105                 110

Thr Ala Leu Trp Ala Phe Gly Leu Thr Asp Glu Val Phe Ala Ala Ala
        115                 120                 125

Thr Thr Lys Leu Met Lys Asp Gln Arg Arg Trp Ser Glu Asn Trp Met
    130                 135                 140

Leu Gly Ile Ala Phe Thr Ser Trp Leu Ser Trp Val Ala Gly Thr Ala
145                 150                 155                 160

Ile Gly Ala Met Phe Gly His Gly Pro Leu Glu Asn Tyr Pro Ala Ile
                165                 170                 175

Glu Ala Ser Leu Ser Phe Met Leu Pro Ala Leu Phe Leu Ser Phe Leu
            180                 185                 190

Leu Ala Ser Phe Lys Arg Gln Tyr Ser Leu Thr Val Ile Ala Ser Leu
        195                 200                 205

Thr Gly Ala Leu Leu Gly Val Leu Leu Phe Ser Ile Pro Val Ala Ile
    210                 215                 220

Leu Ala Gly Ile Gly Gly Gly Cys Leu Ala Ala Leu Leu Gln Pro Val
225                 230                 235                 240

Pro Glu Thr Val Ile Glu Asn Asn Glu Ser Asp Lys Glu Glu Pro Lys
                245                 250                 255

Pro
```

```
<210> SEQ ID NO 12
<211> LENGTH: 257
<212> TYPE: PRT
<213> ORGANISM: Yersinia enterocolitica subsp. enterocolitica

<400> SEQUENCE: 12

Met Gln Ser Gln Thr Thr Asp Ser Pro Ser Thr Ala Gln Pro Thr Ala
1               5                   10                  15

Thr Phe Ile Glu Gly Ile Thr Asp Ser Leu Pro Ile Val Ile Gly Tyr
            20                  25                  30

Leu Pro Val Ala Phe Ala Phe Gly Leu Ser Ser Val Lys Leu Gly Phe
        35                  40                  45

Thr Pro Trp Glu Ala Ile Phe Phe Ser Cys Ile Ile Tyr Ala Gly Ala
    50                  55                  60

Ser Gln Phe Val Ile Thr Ala Leu Leu Ser Ala Gly Met Ser Leu Trp
65                  70                  75                  80

Val Ser Ala Leu Thr Val Met Ala Met Asp Val Arg His Ile Leu Tyr
                85                  90                  95

Gly Pro Ala Leu Lys His Arg Ile Val Thr Arg Leu Ser Gly Lys Lys
            100                 105                 110

Thr Ala Leu Trp Ala Phe Gly Leu Thr Asp Glu Val Phe Ala Ala Ala
        115                 120                 125

Thr Thr Lys Leu Met Lys Asp Gln Arg Arg Trp Ser Glu Asn Trp Met
    130                 135                 140

Leu Gly Ile Ala Phe Thr Ser Trp Leu Ser Trp Val Ala Gly Thr Ala
145                 150                 155                 160

Ile Gly Ala Met Phe Gly His Gly Pro Leu Glu Asn Tyr Pro Ala Ile
                165                 170                 175

Glu Ala Ser Leu Ser Phe Met Leu Pro Ala Leu Phe Leu Ser Phe Leu
            180                 185                 190

Leu Ala Ser Phe Lys Arg Gln Tyr Ser Leu Thr Val Ile Ala Ser Leu
        195                 200                 205

Thr Gly Ala Leu Leu Gly Val Leu Leu Phe Ser Ile Pro Val Ala Ile
    210                 215                 220

Leu Ala Gly Ile Gly Gly Gly Cys Leu Ala Ala Leu Leu Gln Pro Val
225                 230                 235                 240

Pro Glu Thr Val Ile Glu Asn Asn Glu Ser Asp Lys Glu Glu Pro Lys
                245                 250                 255

Pro


<210> SEQ ID NO 13
<211> LENGTH: 113
<212> TYPE: PRT
<213> ORGANISM: Yersinia enterocolitica subsp. enterocolitica

<400> SEQUENCE: 13

Met Asn Met Asp Val Val Ile Ile Gly Leu Val Val Gly Thr Val Asn
1               5                   10                  15

Tyr Leu Phe Arg Tyr Leu Pro Leu Arg Leu Gly Pro Ala Arg Lys Gln
            20                  25                  30

Ala Gly Leu Gln Arg Gly Lys Val Ser Leu Leu Leu Asp Ser Ile Gly
        35                  40                  45

Ile Ala Ser Ile Cys Ala Leu Leu Val Val Ser Ser Thr Pro Glu Ile
    50                  55                  60

Val His Thr Pro Gln Lys Leu Ile Pro Thr Leu Ile Gly Phe Leu Val
65                  70                  75                  80
```

```
Ile Cys Gly Cys Phe Tyr Lys Thr Asn Ser Ile Ile Phe Ala Thr Leu
                85                  90                  95

Leu Gly Ala Leu Ser Tyr Gly Leu Thr Phe Lys Leu Leu Met Ile Leu
            100                 105                 110

Ala


<210> SEQ ID NO 14
<211> LENGTH: 113
<212> TYPE: PRT
<213> ORGANISM: Yersinia enterocolitica subsp. enterocolitica

<400> SEQUENCE: 14

Met Asn Met Asp Val Val Ile Ile Gly Leu Val Val Gly Thr Val Asn
1               5                   10                  15

Tyr Leu Phe Arg Tyr Leu Pro Leu Arg Leu Gly Pro Ala Arg Lys Gln
            20                  25                  30

Ala Gly Leu Gln Arg Gly Lys Val Ser Leu Leu Leu Asp Ser Ile Gly
        35                  40                  45

Ile Ala Ser Ile Cys Ala Leu Leu Val Val Ser Ser Thr Pro Glu Ile
    50                  55                  60

Val His Asn Pro Gln Lys Leu Ile Pro Thr Leu Ile Gly Phe Leu Val
65                  70                  75                  80

Ile Cys Gly Cys Phe Tyr Lys Thr Asn Ser Ile Ile Phe Ala Thr Leu
                85                  90                  95

Leu Gly Ala Leu Ser Tyr Gly Leu Thr Phe Lys Leu Leu Met Ile Leu
            100                 105                 110

Ala


<210> SEQ ID NO 15
<211> LENGTH: 252
<212> TYPE: PRT
<213> ORGANISM: Photorhabdus luminescens subsp. laumondii

<400> SEQUENCE: 15

Met Pro Val Ser Asp Thr Ser Ser Pro Leu Thr Ser Lys Lys Ser Ser
1               5                   10                  15

Phe Thr Glu Gly Ile Ile Asp Ser Leu Pro Ile Val Ile Gly Tyr Ile
            20                  25                  30

Pro Val Ala Phe Ala Phe Gly Leu Asn Ala Val Lys Leu Gly Phe Asn
        35                  40                  45

Pro Met Glu Ala Ile Phe Phe Ser Cys Ile Ile Tyr Ala Gly Ala Ser
    50                  55                  60

Gln Phe Val Ile Thr Ala Leu Leu Ser Ala Gly Thr Ser Leu Trp Ile
65                  70                  75                  80

Ser Ala Leu Thr Ile Met Ala Met Asp Val Arg His Ile Leu Tyr Gly
                85                  90                  95

Pro Ser Leu Arg His Arg Ile Lys Asp Lys Leu Thr Glu Lys Lys Thr
            100                 105                 110

Val Ile Trp Ala Phe Gly Leu Thr Asp Glu Val Phe Ala Ala Ala Thr
        115                 120                 125

Ala Lys Leu Ile Lys Asn His Arg Ser Trp Ser Glu Asn Trp Met Val
    130                 135                 140

Ala Ile Ala Ile Cys Ser Trp Leu Ala Trp Gly Ala Gly Thr Ala Ala
145                 150                 155                 160

Gly Ala Phe Leu Gly Asn Gly Tyr Leu Glu Ser Tyr Pro Ala Ile Glu
```

```
                165                 170                 175

Ala Ala Met Ile Phe Met Leu Pro Ala Leu Phe Leu Ser Phe Leu Leu
            180                 185                 190

Ala Ser Cys Arg Lys Gln Asn Ser Tyr Cys Val Ala Thr Ala Leu Thr
        195                 200                 205

Gly Ala Leu Leu Gly Ile Thr Phe Phe Ser Ile Pro Val Ala Ile Leu
    210                 215                 220

Ala Gly Ile Val Gly Gly Cys Ile Ala Ala Leu Leu Gln Pro Gln Asn
225                 230                 235                 240

Asn Cys Asn Asp Ser Ser Glu Gln Lys Glu Thr Pro
                245                 250


<210> SEQ ID NO 16
<211> LENGTH: 112
<212> TYPE: PRT
<213> ORGANISM: Photorhabdus luminescens subsp. laumondii

<400> SEQUENCE: 16

Met Ile Asp Ser Lys Ile Leu Leu Ile Gly Leu Phe Val Gly Leu Ala
1               5                   10                  15

Asn Phe Ser Phe Arg Tyr Leu Pro Leu Arg Phe Gly Lys Ala Arg Gln
            20                  25                  30

Ser Ala Gly Arg Lys Ala Gly Lys Thr Ser Ile Ile Leu Asp Ser Ile
        35                  40                  45

Gly Ile Ala Ser Ile Cys Ser Leu Leu Ile Val Ser Gly Val Pro Asp
    50                  55                  60

Val Met Arg Glu Ser Gln Lys Leu Leu Pro Thr Leu Ile Gly Cys Leu
65                  70                  75                  80

Thr Ile Cys Leu Val Phe Tyr Lys Thr Lys Gln Ile Ile Leu Ala Thr
                85                  90                  95

Leu Phe Gly Ala Leu Leu Phe Gly Leu Thr Phe Lys Ile Phe Met Asn
            100                 105                 110


<210> SEQ ID NO 17
<211> LENGTH: 245
<212> TYPE: PRT
<213> ORGANISM: Citrobacter youngae

<400> SEQUENCE: 17

Met Asp Ser Pro Ile Pro Gln Ser Gly Ser Arg Ser Ala Thr Leu Thr
1               5                   10                  15

Glu Gly Phe Lys Asp Ser Leu Pro Ile Val Ile Ser Tyr Ile Pro Val
            20                  25                  30

Ala Phe Ala Phe Gly Leu Asn Ala Thr Arg Leu Gly Phe Thr Pro Val
        35                  40                  45

Glu Ser Val Phe Leu Ser Cys Ile Ile Tyr Ala Gly Ala Ser Gln Phe
    50                  55                  60

Val Ile Thr Thr Met Leu Ala Ala Gly Ser Ser Leu Trp Val Ala Ala
65                  70                  75                  80

Leu Thr Val Met Ala Met Asp Val Arg His Val Leu Tyr Gly Pro Ser
                85                  90                  95

Leu Arg Ser Arg Ile Ala Gln Arg Leu Ser Lys Pro Lys Ser Ala Leu
            100                 105                 110

Trp Ala Phe Gly Leu Thr Asp Glu Val Phe Ala Ala Ala Thr Ala Lys
        115                 120                 125

Leu Val Arg Asp Asn Arg Arg Trp Ser Glu Asn Trp Met Ile Gly Ile
```

```
    130                 135                 140

Ala Leu Cys Ser Trp Ala Ser Trp Val Phe Gly Thr Ala Ile Gly Ala
145                 150                 155                 160

Phe Ser Gly Ser Gly Leu Leu Lys Asp Tyr Pro Ala Val Glu Ala Ala
                165                 170                 175

Leu Gly Phe Met Leu Pro Ala Leu Phe Met Ser Phe Leu Leu Ala Ser
            180                 185                 190

Phe Gln Arg Lys Gln Ala Leu Cys Val Thr Val Ala Leu Thr Gly Ala
        195                 200                 205

Leu Ala Gly Val Ile Leu Phe Ser Ile Pro Ala Ala Ile Leu Leu Gly
    210                 215                 220

Ile Val Cys Gly Cys Leu Thr Ala Leu Leu Gln Ser Phe Trp Gln Gly
225                 230                 235                 240

Gly Pro Asp Glu Leu
                245


<210> SEQ ID NO 18
<211> LENGTH: 111
<212> TYPE: PRT
<213> ORGANISM: Citrobacter youngae

<400> SEQUENCE: 18

Met Ser Tyr Glu Val Leu Leu Leu Gly Leu Leu Val Gly Cys Val Asn
1               5                   10                  15

Tyr Cys Phe Arg Tyr Leu Pro Leu Arg Leu Gly Ala Gly Asn Val Arg
            20                  25                  30

Pro Ala Arg Arg Gly Ala Thr Gly Ile Leu Leu Asp Thr Ile Gly Ile
        35                  40                  45

Ala Ser Ile Cys Ala Leu Leu Val Val Ser Thr Ala Pro Glu Val Met
    50                  55                  60

His Asp Ala Arg Arg Phe Val Pro Thr Leu Val Gly Phe Val Ile Leu
65                  70                  75                  80

Gly Ala Ser Phe Tyr Lys Thr Arg Ser Ile Ile Ile Pro Thr Leu Leu
                85                  90                  95

Ser Ala Leu Gly Tyr Gly Leu Ala Trp Lys Met Leu Val Gly Leu
            100                 105                 110


<210> SEQ ID NO 19
<211> LENGTH: 245
<212> TYPE: PRT
<213> ORGANISM: Citrobacter freundii

<400> SEQUENCE: 19

Met Glu Ser Pro Val Pro Gln Ser Glu Ser Ser Ser Ala Thr Leu Thr
1               5                   10                  15

Glu Gly Phe Lys Asp Ser Leu Pro Ile Val Ile Ser Tyr Ile Pro Val
            20                  25                  30

Ala Phe Ala Phe Gly Leu Asn Ala Thr Arg Leu Gly Phe Thr Pro Val
        35                  40                  45

Glu Ser Val Phe Phe Ser Cys Ile Ile Tyr Ala Gly Ala Ser Gln Phe
    50                  55                  60

Val Ile Thr Thr Met Leu Ala Ala Gly Ser Ser Leu Trp Val Ala Ala
65                  70                  75                  80

Leu Thr Val Met Ala Met Asp Val Arg His Val Leu Tyr Gly Pro Ser
                85                  90                  95

Leu Arg Ser Arg Ile Ala Gln Arg Leu Ser Lys Pro Lys Ser Ala Leu
```

```
            100                 105                 110

Trp Ala Phe Gly Leu Thr Asp Glu Val Phe Ala Ala Ala Thr Ala Lys
        115                 120                 125

Leu Val Arg Asp Asn Arg Arg Trp Ser Glu Asn Trp Met Ile Gly Ile
    130                 135                 140

Ala Leu Cys Ser Trp Ala Ser Trp Val Phe Gly Thr Val Leu Gly Ala
145                 150                 155                 160

Phe Ser Gly Ser Gly Leu Leu Lys Asp Tyr Pro Ala Val Glu Ala Ala
                165                 170                 175

Leu Gly Phe Met Leu Pro Ala Leu Phe Met Ser Phe Leu Leu Ala Ser
            180                 185                 190

Phe Gln Arg Lys Gln Ala Leu Cys Val Thr Ala Ala Leu Ala Gly Ala
        195                 200                 205

Leu Ala Gly Val Met Leu Phe Ser Ile Pro Ala Ala Ile Leu Ala Gly
    210                 215                 220

Ile Val Cys Gly Cys Leu Thr Ala Leu Ile Gln Ser Phe Trp Gln Gly
225                 230                 235                 240

Gly Pro Asp Glu Leu
                245


<210> SEQ ID NO 20
<211> LENGTH: 111
<212> TYPE: PRT
<213> ORGANISM: Citrobacter freundii

<400> SEQUENCE: 20

Met Ser Tyr Glu Val Leu Leu Leu Gly Leu Leu Val Gly Cys Val Asn
1               5                   10                  15

Tyr Cys Phe Arg Tyr Leu Pro Leu Arg Leu Gly Val Gly Asn Val Arg
            20                  25                  30

Pro Thr Lys Arg Gly Ala Thr Gly Ile Leu Leu Asp Thr Ile Gly Ile
        35                  40                  45

Thr Ser Ile Cys Ala Leu Leu Val Val Ser Thr Ala Pro Glu Val Met
    50                  55                  60

His Asp Ala Arg Arg Phe Val Pro Thr Leu Val Gly Phe Val Ile Leu
65                  70                  75                  80

Gly Ala Ser Phe Tyr Lys Thr Arg Ser Ile Ile Ile Pro Thr Leu Leu
                85                  90                  95

Ser Ala Leu Gly Tyr Gly Leu Ala Trp Lys Met Leu Val Val Leu
            100                 105                 110


<210> SEQ ID NO 21
<211> LENGTH: 100
<212> TYPE: DNA
<213> ORGANISM: Artificial Sequence
<220> FEATURE:
<223> OTHER INFORMATION: Oligonucleotide

<400> SEQUENCE: 21

atgataaaac tttcgaatat caccaaagtg ttccaccagg gcacccgcac catccaggcg      60

ttgaacaacg tcagcctgca tgtaggctgg agctgcttcg                           100


<210> SEQ ID NO 22
<211> LENGTH: 100
<212> TYPE: DNA
<213> ORGANISM: Artificial Sequence
<220> FEATURE:
<223> OTHER INFORMATION: Oligonucleotide
```

<400> SEQUENCE: 22
taccagcctt taacagctcc gccgttaaac actttgtttg ctgcttcgta aacttcgtca 60
gactgataag cctggacgaa catatgaata tcctccttag 100

<210> SEQ ID NO 23
<211> LENGTH: 1063
<212> TYPE: DNA
<213> ORGANISM: Citrobacter koseri

<400> SEQUENCE: 23
atggaaagcc ctgcacccca gtctgagccc cgtccggcaa cattaacgga aggattcaaa 60
gacagtttac cgatagtcat aagttatatt ccggtggcgt ttgcgtttgg ccttaacgcc 120
acccgtctgg gctttactcc cctcgaaagc gttttttttct cctgcattat ttacgcaggc 180
gccagccagt tcgtcatcac caccatgctc gcggcgggca gcacattatg ggtcgccgcg 240
ctgaccgtga tggcgatgga cgtgcgtcat gtgctgtacg gcccttccct gcgtagtcgc 300
atcagccaac ggctcagtaa acctaaaacc gccctgtggg catttggcct caccgatgaa 360
gtgtttgctg ccgccacggc caaactggtg cgggataacc gccgctggag tgaaaactgg 420
atgatcggca tcgcgttctg ctcctgggcc tcctgggtgc tcggcacggt cattggcgca 480
ttttccggga gcggattgct gaaaggcttc cccgccgttg aggcggcatt aggttttatg 540
ctgccagccc tgtttatgag ctttttgctc gcttcttttc aacgcaaaca aacgctgtgc 600
gtcacggcgg cgttaatcgg cgcgctggca ggcgtcacgc tgttttccat tcctgcggct 660
atcctggcgg gtatcgccag cgggtgtctg accgccttga tccagtcgtt ctggcaagga 720
gcgcccgatg agttatgagg ttctgctgct gggactgctg gtcggctgcg ccaattattg 780
ttttcgttat ttaccgcttc gtctgcgaat gggaaacacc cgccccgcca ggcgcggcgc 840
aacgggcgtg ttgctcgaca ccattggcat cgcgtccatc tgcgccctgc tggtggtgtc 900
tacggctccc gaagtgatgc acgacgccag ccggttcatt ccgacgctgg tcgggtttgc 960
cgtcctgggc gtcagtttct acaagacgcg cagcatcatc atcccaacgc tactgagcgc 1020
tctgggctat ggactcgcct ggaagataga ggtcatttta taa 1063

<210> SEQ ID NO 24
<211> LENGTH: 1063
<212> TYPE: DNA
<213> ORGANISM: Shigella flexneri

<400> SEQUENCE: 24
atggaaagcc ctgttcccca gtctgaatcc cgttctgcaa cgttaactga aggattcaaa 60
gacagcctac cgatagttat cagttatatt ccggtcgcat ttgcatttgg tatgaatgcg 120
actcgcctgg gctttactcc cgttgaaagc gttttttttct cctgcatcat ttacgctggc 180
gccagccagt ttgtcatcac aaccatgctc gccgcaggca gctcactgtg ggtcgcggct 240
ctgaccgtca tggcgatgga tgttcgccat gttttgtacg gcccttctct gcgcagccgt 300
atcgcccgac agctgagcaa acctaaaagc gcgctatggg cctttggcct caccgacgaa 360
gtctttgccg cggcaacggc caagctggtg cgggataacc ggcgctggag tgaaaactgg 420
atgatcggca tcgcgctatg ctcctgggct tcctgggtac ttggtacggt tatcggcgca 480
ttttccggca ctggcttact gaagggattc ccggcggtag aagcggcgct ggggtttatg 540
ctcccggcgc tgtttatgag ttttctgctg gcctctttcc agcgtaatca aacgctatgc 600

-continued

```
gtcacggcgg ctttagccgg tgcgctggct ggcgtgacgc tgttttctat cccggcagcc    660

atcctcgcag gcatagtctg cggatgcctg accgcgctca ttcagtcgtt ctggcaggga    720

ggtcctgatg agttatgagg ttctgctgct cggcctgctg gtcggctgcg tcaattactg    780

ttttcgctat ttaccactgc gtctgcgaat ggggaatgtg cgcccgacaa aacgcggagc    840

cactggaata ctactcgaca ccatcggtat tgcatcaatt tgcgccctgc tagtggtgtc    900

tactgcgcca gaagtgatgc acgatgcccg tcgttttgtg cctacgctgg tggggtttgt    960

ggtactgggt gcaagcttct ataagacccg cagcatcatc attccgacct tactgagtgc   1020

cctgggctat ggattagcct ggaaaatgct gtttgtctta tag                    1063
```

<210> SEQ ID NO 25
<211> LENGTH: 1060
<212> TYPE: DNA
<213> ORGANISM: Raoultella ornithinolytica

<400> SEQUENCE: 25

```
atggaaaaac cggcaccggc aagcgaagca accctgccgg aaggtattaa agatagcctg     60

ccgattgtga ttagctatat tccggttgca tttgcctttg gtctgaatgc aacccgtctg    120

ggttttacac cgctggaaag cctgtttttt agctgtatta tctatgccgg tgcaagccag    180

tttgttatta ccgcaatgct ggcagcaggt agcagcctgt gggttgcagc actgaccgtt    240

atggcaatgg atgttcgtca tgttctgtat ggtccgagcc tgcgtagccg tattcatcgt    300

gcactggata aacgtaaaac cgcactgtgg gcatttggcc tgaccgatga agtttttgca    360

gcagcaaccg caaaactggt tcgtgataat cgtcgttgga gcgaaagctg gatgctgggt    420

attgcattta ccagctggat tagctgggtt tttggcaccc tgattggtgc atatagcggt    480

agcggtctgc tggttggttt tccggcagtt gaagcagccc tgagctttat gctgcctgca    540

ctgtttatga gttttctgct ggcaagcttt cagcgtaaac agagcctgag cgttaccgca    600

gcactggcag gcgcactggg tggtattatt ctgtttagca ttccggcagc aattctggca    660

ggtattgttt gtggttgtct ggcagcgctg attcaggcaa gcattcaggg tatgccggat    720

gaacaataac gttctgatta ttggtattgt ggtgggctgt gtgaattacc tgtttcgtta    780

tctgccgctg cgtctgcgtg caggtaatgc acgtccgacc cgtcgtggtc cgctgagcgt    840

tctgctggat accattggca ttgcaagcat ttgtgcactg ctgattgtta gcagcgttcc    900

ggaaattctg agcgatagcc gtcgtctgct gccgaccctg gttggtttta ccgttctggg    960

tctggcattt tggaaaaccc gtagcattat tatgccgaca ctgctgagcg cactggccta   1020

tggtattgca tggaaaatta ccacctttct gtatttttga                         1060
```

<210> SEQ ID NO 26
<211> LENGTH: 1078
<212> TYPE: DNA
<213> ORGANISM: Enterobacter sp. (R4-368)

<400> SEQUENCE: 26

```
atggatatgg atagcagcgt taccgcaacc aaaagcacca gcgatcagag cgcaaccttt     60

ctggaaggta ttaaagatag cctgccgatt gttctgagct atgttccggt tgcatttgcc    120

tttggtatga atgcaaccaa actgggtttt acaccgctgg aaagcgtgtt ttttagctgt    180

attatctatg ccggtgcaag ccagtttgtt attaccacca tgctggcagc aggtagcgca    240

ctgtgggttg cagcactgac cgttatggca atggatgttc gtcatgttct gtatggtccg    300

agcctgcgta gccgtattct gcagccgctg aaaaatcgta aaaccgcagt gtgggcattt    360
```

ggtctgaccg atgaagtttt tgcagcagca accgcaaaac tggttcgtga taatcgtcgt 420
tggagcgaaa attggatgat tggtattgca ctgtttagct ggctgagctg ggttgccggt 480
acagttctgg gtgcatttag cggtgatggt ctgctggatg gttatccggc agttgaaagt 540
gcactgggct ttatgctgcc tgccctgttt atgagctttc tgctggcaag ctttcagcgt 600
cgtcagatta gcgcagttac cgcagcactg ctgggtgcac tggcaggcgt taccctgttt 660
agcattccgg cagcaattct ggcaggcatt tttgcaggtt gtctggcagc actggttcag 720
gccttttatc agggtgcaag tgatgcgcaa tgaggttctg ctgctgggcc tgctggttgg 780
ttgtgttaat tttctgtttc gttatctgcc gctgcgtatt cgtgcaggtc agagccgtcc 840
ggcaaaacgt ggtgttagcg gtgtttttct ggataccatt ggcattgcaa gcatttgtgc 900
cctgctggta gttagctgtg ttccggaaat tgcagcagat agccgtcgtc tgctgccgac 960
cctggcaggt tttgcagtgc tgggtgttag cttttggaaa acccgtagca ttattctgcc 1020
gacactgctg agcgcatttg cgtatggtat tgtttggaaa ctgctggcag atgcctaa 1078

<210> SEQ ID NO 27
<211> LENGTH: 1112
<212> TYPE: DNA
<213> ORGANISM: Yersinia enterocolitica subsp. enterocolitica

<400> SEQUENCE: 27
atgcaaagcc aaaccaccga ctccccctcg acggcccagc cgaccgccac ctttattgaa 60
ggaataaccg atagcctacc gattgttatc ggttatctac ccgttgcttt tgcctttggt 120
ttgagttcgg taaaacttgg ctttactccg tgggaagcta ttttcttttc ttgcattatt 180
tatgccggag ccagccaatt cgttattacc gccctgctca gcgcggggat gtcattgtgg 240
gtttccgcct tgaccgtgat ggctatggat gtccgccata tcttgtacgg gccagcactg 300
aaacaccgca ttgtaaccag gttatctggc aaaaaaacgg cgctgtgggc ctttggtctt 360
actgatgaag tgtttgccgc cgcaacaacc aagctaatga aagatcaacg gcgctggagt 420
gaaaactgga tgcttggcat cgcgttcacc tcttggttgt cttgggtagc tggcaccgct 480
atcggcgcga tgtttggtca tgggccgctg gaaaattacc cggcgattga agcatcactc 540
tcctttatgc tcccggcgct attcctcagc ttcttattgg cctcgttcaa acgccaatac 600
agccttaccg ttattgcttc actgaccgga gccttgctgg gcgtgctgct gttctctatt 660
ccggtggcta ttttagccgg tattggcggc ggatgcctgg cagccctgct ccaacccgtc 720
cccgagaccg ttatagaaaa taacgagagt gataaagagg agccgaagcc atgaatatgg 780
atgttgtgat cattggtttg gtggtgggaa cggtcaatta cctgtttcgt tatctgccgc 840
tgcgcctggg gcctgcccgt aaacaagcag gcctgcaacg agggaaagtc tccctgttgc 900
tagacagcat cgggatcgcc tctatctgtg cgttgttggt ggtttccagt accccggaga 960
tagtgcataa cccacagaaa ttaattccta cactaattgg ttttttagtt atctgtggat 1020
gcttttataa aaccaacagt attatcttcg ccaccttact gggagcactc agttacggtc 1080
tgacattcaa attactgatg attttggcat aa 1112

<210> SEQ ID NO 28
<211> LENGTH: 1094
<212> TYPE: DNA
<213> ORGANISM: Photorhabdus luminescens subsp. laumondii

<400> SEQUENCE: 28

-continued

```
atgcctgttt ctgatacatc atccccctta acgagtaaaa aatcttcttt tactgaagga     60
ataatagata gtttacccat tgttatcggt tatattcccg tcgcctttgc ttttggtctc    120
aatgccgtca aacttggctt caacccaatg gaagccattt tcttttcatg catcatctac    180
gccggtgcaa gccagttcgt catcacagct ttactgagtg cggggacatc attatggatt    240
tctgccctaa caattatggc aatggatgtc cgccatattc tttatggtcc atctttaagg    300
caccgtatca aagataagct aacggagaaa aaaaccgtta tctgggcttt cggcctgaca    360
gatgaagttt ttgccgccgc gactgcaaaa ctcattaaaa accaccggag ctggagtgaa    420
aactggatgg ttgctattgc aatctgttct tggctggcct ggggcgcagg taccgcagcc    480
ggtgcatttc ttggtaacgg ttatttggaa tcctatcccg ctatagaagc tgccatgatt    540
ttcatgttac cagcactatt tctcagtttt cttcttgctt cttgtagaaa acaaaatagt    600
tattgtgttg caaccgcact aaccggagca cttttaggga ttacattttt ctcaattcca    660
gttgctattc tggcaggtat tgtcggtggt tgtatcgcgg cactgttaca accgcaaaac    720
aattgcaatg actcttcaga acaaaaggaa acaccatgat tgatagcaag attttgctga    780
ttggactatt tgttgggtta gctaactttt catttcgcta tctgccacta cgatttggga    840
aagcacgcca atctgccggc agaaaagctg gaaaaacaag cattatcctt gacagtattg    900
gtattgcatc catttgttct ttactcatcg tatcaggtgt acctgatgtg atgagagaaa    960
gtcaaaaact acttcctacc ctcataggtt gtctgaccat ctgtttagtc ttttacaaaa   1020
caaagcaaat tatactcgca acactatttg gcgcactgct tttggacta acattcaaaa   1080
tatttatgaa ttag                                                     1094
```

<210> SEQ ID NO 29
<211> LENGTH: 1063
<212> TYPE: DNA
<213> ORGANISM: Citrobacter youngae

<400> SEQUENCE: 29

```
atggatagcc cgattccgca gagcggtagc cgtagcgcaa ccctgaccga aggttttaaa     60
gatagcctgc cgattgtgat tagctatatt ccggttgcat ttgcctttgg tctgaatgca    120
acccgtctgg gttttacacc ggttgaaagc gtttttctga gctgtattat ctatgccggt    180
gcaagccagt ttgttattac caccatgctg gcagcaggta gcagcctgtg ggttgcagca    240
ctgaccgtta tggcaatgga tgttcgtcat gttctgtatg gtccgagcct gcgtagccgt    300
attgcacagc gtctgagcaa accgaaaagc gcactgtggg catttggcct gaccgatgaa    360
gtttttgcag cagcaaccgc aaaactggtt cgtgataatc gtcgttggag cgaaaattgg    420
atgattggta ttgcactgtg tagctgggca agctgggttt ttggcaccgc aattggtgca    480
tttagcggta gcggtctgct gaaagattat ccggcagttg aagcagcact gggctttatg    540
ctgcctgcac tgtttatgag ctttctgctg gcgagctttc agcgtaaaca ggcactgtgt    600
gttaccgttg ccctgaccgg tgcactggca ggcgttattc tgtttagcat tccggcagca    660
attctgctgg gtattgtttg tggttgtctg accgcactgc tgcagagctt ttggcagggt    720
ggtccggatg agctatgagg ttctgctgct gggtctgctg gttggttgtg tgaattattg    780
ttttcgttat ctgccgctgc gtctgggtgc aggtaatgtt cgtccggcac gtcgtggtgc    840
aaccggtatc ctgctggata caattggcat tgcaagcatt tgtgcactgc tggtagttag    900
caccgcaccg gaagttatgc atgatgcacg tcgttttgtt ccgaccctgg tgggttttgt    960
tattctgggt gccagcttct ataaaacccg tagcattatt atcccgaccc tgctgagcgc   1020
```

-continued

```
actgggttat ggtctggcat ggaaaatgct ggtaggtctg taa                 1063


<210> SEQ ID NO 30
<211> LENGTH: 1063
<212> TYPE: DNA
<213> ORGANISM: Citrobacter freundii

<400> SEQUENCE: 30

atggaaagtc cggttccgca gagcgaaagc agcagcgcaa ccctgaccga aggttttaaa    60

gatagcctgc cgattgtgat tagctatatt ccggttgcat ttgcctttgg tctgaatgca   120

acccgtctgg gttttacacc ggttgaaagc gtgtttttta gctgcattat ctatgccggt   180

gcaagccagt ttgttattac caccatgctg gcagcaggta gcagcctgtg ggttgcagca   240

ctgaccgtta tggcaatgga tgttcgtcat gttctgtatg gtccgagcct gcgtagccgt   300

attgcacagc gtctgagcaa accgaaaagc gcactgtggg catttggcct gaccgatgaa   360

gtttttgcag cagcaaccgc aaaactggtt cgtgataatc gtcgttggag cgaaaattgg   420

atgattggta ttgcactgtg tagctgggca agctgggttt ttggcaccgt tctgggtgca   480

tttagcggta gcggtctgct gaaagattat ccggcagttg aagcagcact gggctttatg   540

ctgcctgcac tgtttatgag ctttctgctg gcgagctttc agcgtaaaca ggcactgtgt   600

gttaccgcag ccctggcagg cgcactggct ggtgttatgc tgtttagcat tccggcagca   660

attctggcag gtattgtttg tggttgtctg accgcactga ttcagagctt ttggcagggt   720

ggtccggatg agctatgaag ttctgctgct gggtctgctg gttggttgtg tgaattattg   780

ttttcgttat ctgccgctgc gtctgggtgt tggtaatgtt cgtccgacca aacgtggtgc   840

aaccggtatt ctgctggata ccattggtat taccagcatt tgtgcactgc tggtagttag   900

caccgcaccg gaagttatgc atgatgcacg tcgttttgtt ccgaccctgg tgggttttgt   960

tatcctgggt gccagcttct ataaaacccg tagcattatt atcccgaccc tgctgagcgc  1020

actgggttat ggtctggcat ggaaaatgct ggttgttctg taa                 1063
```

MICROORGANISM FOR METHIONINE PRODUCTION WITH ENHANCED METHIONINE EFFLUX

FIELD OF THE INVENTION

The present invention relates to a recombinant microorganism useful for the production of L-methionine and/or its derivatives and process for the preparation of L-methionine. The microorganism of the invention is modified in a way that the methionine/carbon source yield is increased by combining the attenuation of the L-methionine uptake system to the overexpression of a specific export system. In particular, the operon metNIQ is deleted and the genes ygaZ and ygaH or their homologous genes are overexpressed in the recombinant microorganism.

PRIOR ART

Sulphur-containing compounds such as cysteine, homocysteine, methionine or S-adenosylmethionine are critical to cellular metabolism. In particular L-methionine, an essential amino acid, which cannot be synthesized by animals, plays an important role in many body functions. Most of the methionine produced industrially is widely used as an animal feed and food additive.

With the decreased use of animal-derived proteins as a result of BSE and chicken flu, the demand for pure methionine has increased. Commonly, D,L-methionine is produced chemically from acrolein, methyl mercaptan and hydrogen cyanide. However, the racemic mixture does not perform as well as pure L-methionine (Saunderson, 1985). Additionally, although pure L-methionine can be produced from racemic methionine, for example, through the acylase treatment of N-acetyl-D,L-methionine, this dramatically increases production costs. Accordingly, the increasing demand for pure L-methionine coupled with environmental concerns render microbial production of methionine an attractive prospect.

Other important amino acids, such as lysine, threonine and tryptophan are produced via fermentation for use in animal feed. Therefore, these amino acids can be made using glucose and other renewable resources as starting materials. Industrial production of L-methionine via fermentation has not been successful yet, but the development of the technology is on going.

Different approaches for the optimisation of L-methionine production in microorganisms have been described previously (see, for example, Patents or patent applications U.S. Pat. Nos. 7,790,424, 7,611,873, WO 2002/10209, WO 2005/059093 and WO 2006/008097); however, industrial production of L-methionine from microorganisms requires further improvements.

When L-methionine is synthesized at a certain level or higher, it inhibits its own further production via feedback loop and disturbs the physiology of the cell. Therefore one of these improvements is to reduce the L-methionine accumulation into the microorganism to ensure an efficient production by reducing the L-methionine import capability of the microorganism while enhancing the L-methionine efflux at the same time in a recombinant L-methionine overproducer.

Early biochemical and kinetic studies demonstrated that methionine uptake in *Escherichia coli* involves at least two specific transporters: the high-affinity MetD and low-affinity MetP transport systems (Jones & George, 1999; Kadner, 1974). Both are regulated by the internal methionine pool size and, for MetD, MetJ-mediated repression has been inferred (Kadner, 1975; Kadner & Winkler, 1975). The MetD methionine uptake system was characterized as an ABC transporter. In 2002, Merlin et al, report that the genes abc, yaeC, and yaeE comprise metD, the locus encoding a methionine uptake system. They propose to rename abc, yaeE, and yaeC as metN, metI, and metQ, respectively.

Methionine export is mediated, in *Escherichia coli* by the complex YgaZH and in *Corynebacterium glutamicum* by the homologous complex BrnFE (Trötschel et al., 2005). YgaZ is a member of the branched chain amino acid exporter (LIV-E) family responsible for export of L-valine and L-methionine. YgaZ forms a complex with YgaH, a predicted inner membrane protein, to export amino-acids under conditions in which theirs levels would be toxic to the cell.

Patent applications WO 2002/097096 and WO 2005/085463 relate to reduction of the L-methionine uptake in *Coynebacterium* by attenuating the MetD2 methionine uptake system, especially by deleting one or more of the genes yaeC, abc and yaeE. In *Corynebacterium*, the attenuation of the MetD2 methionine uptake system leads to an improved production of methionine. The homologous MetD methionine uptake system, encoded by the metN, metI and metQ genes, has been also characterized in *Escherichia coli* (Jones & George, 1999; Kadner 1974, Merlin et al., 2002). Patent application WO 2008/127240 discloses that in *Escherichia coli* as in *Corynebacterium* the methionine production is increased when MetD methionine uptake system is attenuated.

Patent applications EP 1239041 and WO 2008/082211 describe the overexpression of a branched chain amino acid exporter (YgaZH) responsible for the export of L-valine and L-methionine in *Escherichia coli*. This overexpression leads to an improved production of methionine in *E. coli.*

Trötschel et al. overexpressed in *Corynebacterium glutamicum* brnF and brnE genes encoding the BrnFE methionine exporter and in the same time deleted the metD system (Trötschel et al., 2005). Nevertheless any evidence of the impact of these modifications on the methionine production in *Corynebacterium glutamicum* neither in *Escherichia coli* has been published.

Unlike prior art on *C. glutamicum* and on *E. coli*, inventors have shown that the deletion of only metD in *E. coli* (achieved either by the deletion of one of the gene from the operon metNIQ or by the deletion of the entire operon, deletion of any single gene of this operon leading to abolishment of high affinity methionine uptake) is not sufficient to improve the methionine production performances. This modification must be combined to the overexpression of an L-methionine export system.

This is then the first time that the combination of the deletion of the L-methionine uptake system with the overexpression of an L-methionine export is shown as being beneficial for the methionine production.

SUMMARY OF THE INVENTION

The invention relates to a recombinant *Escherichia coli* strain and method for optimising the production of methionine and/or its derivatives, wherein the methionine import is attenuated and the methionine efflux is enhanced. In the recombinant microorganism, methionine import is attenuated by attenuating the expression or deleting at least one gene chosen among metN, metI or metQ whereas methionine efflux is enhanced by overexpressing the genes ygaZH or their homologous genes.

The recombinant microorganism may also comprise other genetic modifications such as:

an increased expression of at least one of the following genes: ptsG, pyc, pntAB, cysP, cys U, cys W, cysA, cysM, cysJ, cysI, cysH, gcvT, gcvH, gcvP, lpd, serA, serB, serC, cysE, metF, metH, fldA, fpr, metA, metA* allele encoding for an enzyme with reduced feed-back sensitivity to S-adenosylmethionine and/or methionine, thrA, or a thrA* allele encoding for an enzyme with reduced feed-back inhibition to threonine and/or an attenuated expression of one of the following genes: metJ, pykA, pykF, purU, ybdL, udhA, dgsA, metE or yncA.

In a particular embodiment, the present invention is related to a recombinant microorganism wherein: a) the genes metN, metI and metQ are deleted whereas the genes ygaZ and ygaH or their homologous genes originating from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii* are overexpressed, and b) the expression of the genes metA*, metH, cysPUWAM, cysJIH, gcvTHP, metF, serA, serB, serC, cysE, thrA* and pyc are enhanced; and c) the expression of the genes metJ, pykA, pykF, purU, ybdL, yncA, dgsA, metE and udhA are attenuated.

DETAILED DESCRIPTION OF THE INVENTION

Before describing the present invention in detail, it is to be understood that this invention is not limited to particularly exemplified methods and may, of course, vary. It is also to be understood that the terminology used herein is for the purpose of describing particular embodiments of the invention only, and is not intended to be limiting, which will be limited only by the appended claims.

All publications, patents and patent applications cited herein, whether supra or infra, are hereby incorporated by reference in their entirety.

Furthermore, the practice of the present invention employs, unless otherwise indicated, conventional microbiological and molecular biological techniques within the skill of the art. Such techniques are well known to the skilled worker, and are explained fully in the literature.

It must be noted that as used herein and in the appended claims, the singular forms "a", "an", and "the" include plural reference unless the context clearly dictates otherwise. Thus, for example, a reference to "a microorganism" includes a plurality of such microorganisms, and a reference to "an endogenous gene" is a reference to one or more endogenous genes, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

In the claims that follow and in the consecutive description of the invention, except where the context requires otherwise due to express language or necessary implication, the word "comprise", "contain", "involve" or "include" or variations such as "comprises", "comprising", "containing", "involved", "includes", "including" are used in an inclusive sense, i.e. to specify the presence of the stated features but not to preclude the presence or addition of further features in various embodiments of the invention.

The term "methionine" and "L-methionine" designate the essential sulphur-containing amino-acid with chemical formula $HO_2CCH(NH_2)CH_2CH_2SCH_3$ and CAS number 59-51-8 or 63-68-3 for the specific L-isomer.

"Derivatives of methionine" refers to molecules analogs to methionine which present the same chemical backbone but differ from methionine with at least one chemical group. In this invention, preferred methionine derivatives are N-acetyl methionine (NAM), S-adenosyl methionine (SAM) and hydroxy-methionine (or methionine hydroxy analogue or MHA).

The term "microorganism", as used herein, refers to a bacterium, yeast or fungus which is not modified artificially. Preferentially, the microorganism is selected among *Enterobacteriaceae, Bacillaceae, Streptomycetaceae* and *Corynebacteriaceae*. More preferentially the microorganism is a species of *Escherichia, Klebsiella, Pantoea, Salmonella*, or *Corynebacterium*. Even more preferentially the microorganism of the invention is either the species *Escherichia coli* or *Corynebacterium glutamicum*.

The term "recombinant microorganism" or "genetically modified microorganism", as used herein, refers to a bacterium, yeast or fungus that is not found in nature and is genetically different from its equivalent found in nature. It means, it is modified either by introduction or by deletion or by modification of genetic elements. It can also be transformed by forcing the development and evolution of new metabolic pathways by combining directed mutagenesis and evolution under specific selection pressure (see, for example, WO 2004/076659 or WO 2007/011939).

A microorganism may be modified to express exogenous genes if these genes are introduced into the microorganism with all the elements allowing their expression in the host microorganism. The modification or "transformation" of microorganisms with exogenous DNA is a routine task for those skilled in the art.

A microorganism may be modified to modulate the expression level of an endogenous gene.

The term "endogenous gene" means that the gene was present in the microorganism before any genetic modification. Endogenous genes may be overexpressed by introducing heterologous sequences in addition to, or to replace endogenous regulatory elements, or by introducing one or more supplementary copies of the gene into the chromosome or a plasmid. Endogenous genes may also be modified to modulate their expression and/or activity. For example, mutations may be introduced into the coding sequence to modify the gene product or heterologous sequences may be introduced in addition to or to replace endogenous regulatory elements. Modulation of an endogenous gene may result in the up-regulation and/or enhancement of the activity of the gene product, or alternatively, down regulate and/or lower the activity of the endogenous gene product.

Another way to modulate their expression is to exchange the endogenous promoter of a gene (e.g., wild type promoter) with a stronger or weaker promoter to up or down regulate expression of the endogenous gene. These promoters may be homologous or heterologous. It is well within the ability of the person skilled in the art to select appropriate promoters.

Contrariwise, "exogenous gene" means that the gene was introduced into a microorganism, by means well known by the man skilled in the art whereas this gene is not naturally occurring in the microorganism. Exogenous genes may be integrated into the host chromosome, or be expressed extrachromosomally by plasmids or vectors. A variety of plasmids, which differ with respect to their origin of replication and their copy number in the cell, are well known in the art. These genes may be homologous.

In the context of the invention, the term "homologous gene" is not limited to designate genes having a theoretical common genetic ancestor, but includes genes which may be genetically unrelated that have, none the less, evolved to encode protein which perform similar functions and/or have similar structure. Therefore the term 'functional homolog' for the purpose of the present invention relates to the fact that a certain enzymatic activity may not only be provided by a specific protein of defined amino acid sequence, but also by proteins of similar sequence from other (un)related microorganisms.

Using the references given in Genbank for known genes, those skilled in the art are able to determine the equivalent genes in other organisms, bacterial strains, yeast, fungi, mammals, plants, etc. This routine work is advantageously done using consensus sequences that can be determined by carrying out sequence alignments with genes derived from other microorganisms and designing degenerate probes to clone the corresponding gene in another organism. These routine methods of molecular biology are well known to those skilled in the art.

The terms "improved methionine production", "improve methionine production" and grammatical equivalents thereof, as used herein, refer to an increased methionine/carbon source yield (ratio of gram/mol methionine produced per gram/mol carbon source consumed that it can be expressed in percent). Methods for determining the amount of carbon source consumed and of methionine produced are well known to those in the art. The yield is higher in the recombinant microorganism compared to the corresponding unmodified microorganism.

The terms "microorganism optimised for the fermentative production of methionine" refers to microorganisms evolved and/or genetically modified to present an improved methionine production in comparison with the endogenous production of the corresponding wild-type microorganisms. Such microorganisms "optimised" for methionine production are well known in the art, and have been disclosed in particular in patent applications WO 2005/111202, WO 2007/077041, WO 2009/043803 and WO 2012/098042.

According to the invention the terms "fermentative production", "culture" or "fermentation" are used to denote the growth of bacteria. This growth is generally conducted in fermenters with an appropriate culture medium adapted to the microorganism being used and containing at least one simple carbon source, and if necessary co-substrates.

An "appropriate culture medium" designates a medium (e.g., a sterile, liquid media) comprising nutrients essential or beneficial to the maintenance and/or growth of the cell such as carbon sources or carbon substrates, nitrogen sources, for example, peptone, yeast extracts, meat extracts, malt extracts, urea, ammonium sulfate, ammonium chloride, ammonium nitrate and ammonium phosphate; phosphorus sources, for example, monopotassium phosphate or dipotassium phosphate; trace elements (e.g., metal salts), for example magnesium salts, cobalt salts and/or manganese salts; as well as growth factors such as amino acids and vitamins.

The term "carbon source" or "carbon substrate" or "source of carbon" according to the present invention denotes any source of carbon that can be used by those skilled in the art to support the normal growth of a microorganism, including monosaccharides (such as glucose, galactose, xylose, fructose or lactose), oligosaccharides, disaccharides (such as sucrose, cellobiose or maltose), molasses, starch or its derivatives, hemicelluloses and combinations thereof. An especially preferred simple carbon source is glucose. Another preferred simple carbon source is sucrose. The carbon source can be derived from renewable feed-stock. Renewable feed-stock is defined as raw material required for certain industrial processes that can be regenerated within a brief delay and in sufficient amount to permit its transformation into the desired product. Vegetal biomass treated or not, is an interesting renewable carbon source.

The term "source of sulphur" according to the invention refers to sulphate, thiosulfate, hydrogen sulphide, dithionate, dithionite, sulphite, methylmercaptan, dimethylsulfide and other methyl capped sulphides or a combination of the different sources. More preferentially, the sulphur source in the culture medium is sulphate or thiosulfate or a mixture thereof.

The terms "source of nitrogen" corresponds to either an ammonium salt or ammoniac gas. The nitrogen source is supplied in the form of ammonium or ammoniac.

The terms "attenuation" or "expression attenuated" mean in this context that the expression of a gene or the production of an enzyme is decreased or suppressed compared to the non modified microorganism leading to a decrease in the intracellular concentration of a ribonucleic acid, a protein or an enzyme compared to the non modified microorganism. The man skilled in the art knows different means and methods to measure ribonucleic acid concentration or protein concentration in the cell including for instance use of Reverse Transcription Polymerase Chain Reaction (RT-PCR) and Real-time Polymerase Chain Reaction (qPCR) to determine ribonucleic acid concentration and use of specific antibody to determine concentration of specific protein.

Decrease or suppression of the production of an enzyme is obtained by the attenuation of the expression of gene encoding said enzyme.

Attenuation of genes may be achieved by means and methods known to the man skilled in the art. Generally, attenuation of gene expression may be achieved by:

- Mutating the coding region or the promoter region or,
- Deleting of all or a part of the promoter region necessary for the gene expression or,
- Deleting of all or a part of the coding region of the gene by homologous recombination or,
- Inserting an external element into coding region or into promoter region or,
- Expressing the gene under control of a weak promoter or an inducible promoter.

The man skilled in the art knows a variety of promoters which exhibit different strength and which promoter to use for a weak or an inducible genetic expression.

The term "activity" of an enzyme is used interchangeably with the term "function" and designates, in the context of the invention, the reaction that is catalyzed by the enzyme. The man skilled in the art knows how to measure the enzymatic activity of said enzyme.

The terms "attenuated activity" or "reduced activity" of an enzyme mean either a reduced specific catalytic activity of the protein obtained by mutation in the aminoacids sequence and/or decreased concentrations of the protein in the cell obtained by mutation of the nucleotidic sequence or by deletion of the coding region of the gene.

The terms "enhanced activity" or "increased activity" of an enzyme designate either an increased specific catalytic activity of the enzyme, and/or an increased quantity/availability of the enzyme in the cell, obtained for example by overexpressing the gene encoding the enzyme.

The terms "increased expression", "enhanced expression" or "overexpression" and grammatical equivalents thereof, are used interchangeably in the text and have a similar meaning. These terms mean that the expression of a gene or the production of an enzyme is increased compared to the non modified microorganism leading to an increase in the intracellular concentration of a ribonucleic acid, a protein or an enzyme compared to the non modified microorganism. The man skilled in the art knows different means and methods to measure ribonucleic acid concentration or protein concentration in the cell including for use of Reverse Transcription Polymerase Chain Reaction (RT-PCR) and Real-time Polymerase Chain Reaction (qPCR) to determine ribonucleic acid concentration and use of specific antibody to determine concentration of specific protein.

Increase production of an enzyme is obtained by increasing expression of the gene encoding said enzyme.

To increase the expression of a gene, the man skilled in the art knows different techniques such as:

- Increasing the number of copies of the gene in the microorganism. The gene is encoded chromosomally or extrachromosomally. When the gene is located on the chromosome, several copies of the gene can be introduced on the chromosome by methods of recombination, known by the expert in the field (including gene replacement). When the gene is located extra-chromosomally, it may be carried by different types of plasmids that differ with respect to their origin of replication and thus their copy number in the cell. These plasmids are present in the microorganism in 1 to 5 copies, or about 20 copies, or up to 500 copies, depending on the nature of the plasmid: low copy number plasmids with tight replication (pSC101, RK2), low copy number plasmids (pACYC, pRSF1010) or high copy number plasmids (pSK bluescript II).
- Using a promoter leading to a high level of expression of the gene. The man skilled in the art knows which promoters are the most convenient, for example promoters Ptrc, Ptac, Plac, or the lambda promoter a are widely used. These promoters can be "inducible" by a particular compound or by specific external condition like temperature or light. These promoters may be homologous or heterologous.
- Attenuating the activity or the expression of a transcription repressor, specific or non-specific of the gene.
- Using elements stabilizing the corresponding messenger RNA (Carrier and Keasling, 1999) or elements stabilizing the protein (e.g., GST tags, GE Healthcare).

The terms "encoding" or "coding" refer to the process by which a polynucleotide, through the mechanisms of transcription and translation, produces an amino-acid sequence. The gene(s) encoding the enzyme(s) can be exogenous or endogenous.

The terms "feed-back sensitivity" or "feed-back inhibition" refer to a cellular mechanism control in which an or several enzyme that catalyse the production of a particular substance in the cell are inhibited or less active when that substance has accumulated to a certain level. So the terms "reduced feed-back sensitivity" or "reduced feed-back inhibition" mean that the activity of such a mechanism is decreased or suppressed compared to a non modified microorganism. The man skilled in the art knows how to modify the enzyme to obtain this result. Such modifications have been described in the patent application WO 2005/111202 or in the U.S. Pat. No. 7,611,873.

In a first aspect of the invention, a recombinant *Escherichia coli* strain is optimised for the fermentative production of methionine and/or its derivatives by attenuating the methionine uptake and by enhancing the methionine efflux in said microorganism.

As described above, methionine import is mediated by the MetD methionine uptake system encoded by the metN, metI and metQ genes, formerly named abc, yaeE, and yaeC respectively. These genes have been identified in several microorganisms included *E. coli* and *C. glutamicum*. MetNIQ belongs to the famous ABC-transporter family.

In one embodiment of the invention, the expression of at least one gene chosen among metN, metI and metQ is attenuated in the recombinant microorganism. The man skilled in the art knows different means to attenuate gene expression like cloning the gene to be attenuated under control of an inducible or weak promoter, deleting all or part of the promoter region or coding region of the gene to be attenuated. Preferably, at least one of the genes metN, metI and metQ is deleted. More preferably, the three genes metN, metI and metQ are deleted in the recombinant microorganism of the invention.

In amino-acid producer microorganisms, methionine is excreted by a specific efflux transporter. Notably, in *E. coli*, this transporter is called YgaZH and is encoded by the ygaZ and ygaH genes whereas in *C. glutamicum*, it is named BrnFE and is encoded by the brnF and brnE genes. Functional homologues of this methionine efflux system have been identified in several other microorganisms. Alternatively, the recombinant microorganism of the invention may overexpress functional homologues of YgaZH or BrnFE systems. YgaZ and YgaH homologous protein are presented respectively in Table 1 and Table 2.

TABLE 1

YgaZ homologous proteins

| Acession Number | Name | *Organism* |
|---|---|---|
| YP_001455539.1<br>NC_009792.1.<br>ABV15103.1 | hypothetical protein CKO_04031 [*Citrobacter koseri* ATCC BAA-895] | *Citrobacter koseri* |
| WP_005122932.1<br>EIQ78635.1 | membrane protein [*Shigella flexneri*] | *Shigella flexneri* |
| YP_007877063.1<br>AGJ89511.1<br>WP_015585890.1 | hypothetical protein RORB6_24155 [*Raoultella ornithinolytica* B6] | *Raoultella ornithinolytica* |
| YP_008107733.1<br>AGN85393.1<br>WP_020454909.1 | membrane protein [*Enterobacter* sp. R4-368] | *Enterobacter* sp. |
| WP_004959353.1<br>EFE95945.1 | membrane protein [*Serratia odorifera*] | *Serratia odorifera* |
| YP_003884334.1<br>ADM99777.1 | amino acid transporter [*Dickeya dadantii* 3937] *Erwinia chrysanthemi* (strain 3937) | *Dickeya dadantii* |

TABLE 1-continued

| YgaZ homologous proteins | | |
|---|---|---|
| Acession Number | Name | *Organism* |
| YP_006647984.1 AFR04731.1 | amino acid transporter [*Pectobacterium carotovorum* subsp. *carotovorum* PCC21] | *Pectobacterium carotovorum* subsp. *Carotovorum* |
| YP_001007412.1 CAL13268.1 | putative amino acid transporter [*Yersinia enterocolitica* subsp. *enterocolitica* 8081] | *Yersinia enterocolitica* subsp. *Enterocolitica* |
| NP_928590.1 CAE13573.1 | hypothetical protein plu1279 [*Photorhabdus luminescens* subsp. *laumondii* TTO1] | *Photorhabdus luminescens* subsp. *Laumondii* |
| WP_004847360.1 EHM42581.1 | membrane protein [*Hafnia alvei*] | *Hafnia alvei* |
| WP_016157304.1 EOQ28426.1 | inner membrane protein YgaZ [*Citrobacter* sp. KTE32] | *Citrobacter* sp. KTE32 |
| WP_006687199.1 EFE06904.1 | membrane protein [*Citrobacter youngae*] putative azaleucine resistance protein AzlC [*Citrobacter youngae* ATCC 29220] | *Citrobacter youngae* |
| YP_005198838.1 AEX50698.1 | putative branched-chain amino acid permease (azaleucine resistance) [*Rahnella aquatilis* CIP 78.65 = ATCC 33071] | *Rahnella aquatilis* |
| WP_009111644.1 EHD20336.1. | membrane protein [*Brenneria* sp. EniD312] | *Brenneria* sp. |
| YP_003469114.1 CBJ82350.1 | amino acid transporter [*Xenorhabdus bovienii* SS-2004] | *Xenorhabdus bovienii* |
| WP_000841919.1 | membrane protein [*Shigella flexneri*] | *Shigella flexneri* |
| WP_000445647.1 | membrane protein [*Shigella dysenteriae*] | *Shigella dysenteriae* |
| WP_000445645.1 | membrane protein [*Shigella flexneri*] | *Shigella flexneri* |
| EFP71467.1 | azlC family protein [*Shigella dysenteriae* 1617] | *Shigella dysenteriae* |
| WP_005063865.1 | membrane protein [*Shigella flexneri*] | *Shigella flexneri* |
| WP_001428008.1 | membrane protein [*Shigella dysenteriae*] | *Shigella dysenteriae* |
| WP_005031133.1 | membrane protein [*Shigella dysenteriae*] | *Shigella dysenteriae* |
| WP_004993748.1 | membrane protein [*Shigella boydii*] | *Shigella boydii* |
| WP_005099151.1 | membrane protein [*Shigella flexneri*] | *Shigella flexneri* |
| NP_708495.1 | hypothetical protein SF2709 [*Shigella flexneri* 2a str. 301] | *Shigella flexneri* |
| YP_409184.1. NC_007613.1. ABB67356 | hypothetical protein SBO_2835 [*Shigella boydii* Sb227] | *Shigella boydii* |
| WP_005119769.1 | branched-chain amino acid permease [*Shigella flexneri*] | *Shigella flexneri* |
| WP_003825971.1 | membrane protein [*Citrobacter* sp. 30_2] | *Citrobacter* sp. |
| WP_016154156.1 | inner membrane protein YgaZ [*Citrobacter* sp. KTE151] | *Citrobacter* sp. |
| WP_003839672.1 | hypothetical protein [*Citrobacter freundii*] | *Citrobacter freundii* |
| WP_016150871.1 | inner membrane protein YgaZ [*Citrobacter* sp. KTE30] | *Citrobacter* sp. |
| WP_019077531.1 | membrane protein [*Citrobacter freundii*] | *Citrobacter freundii* |
| WP_003037292.1 | membrane protein [*Citrobacter* sp. L17] | *Citrobacter* sp. |
| WP_009652545.1 | membrane protein [*Klebsiella* sp. OBRC7] | *Klebsiella* sp. |
| WP_004853460.1 | membrane protein [*Klebsiella oxytoca*] | *Klebsiella oxytoca* |
| YP_005016079.1 | AzlC family protein [*Klebsiella oxytoca* KCTC 1686] | *Klebsiella oxytoca* |
| WP_004866792.1 | membrane protein [*Klebsiella oxytoca*] | *Klebsiella oxytoca* |
| WP_017459327.1 | membrane protein [*Enterobacter cloacae*] | *Enterobacter cloacae* |
| WP_004205700.1 | AzlC family protein [*Klebsiella pneumoniae*] | *Klebsiella pneumoniae* |
| CDA02044.1 | azlC family protein [*Klebsiella variicola* CAG:634] | *Klebsiella variicola* |
| WP_004123979.1 | membrane protein [*Klebsiella oxytoca*] | *Klebsiella oxytoca* |
| WP_004132932.1 | azlC family protein [*Klebsiella oxytoca*] | *Klebsiella oxytoca* |
| WP_017900616.1 | membrane protein [*Klebsiella pneumoniae*] | *Klebsiella pneumoniae* |
| YP_002236980.1 | AzlC family protein [*Klebsiella pneumoniae* 342] | *Klebsiella pneumoniae* |
| YP_005228384.1 | putative amino acid transport protein [*Klebsiella pneumoniae* subsp. *pneumoniae* HS11286] | *Klebsiella pneumoniae* subsp. *Pneumoniae* |
| YP_001336647.1 | putative amino acid transport protein [*Klebsiella pneumoniae* subsp. *pneumoniae* MGH 78578] | *Klebsiella pneumoniae* subsp. *Pneumoniae* |
| WP_016947585.1 | membrane protein [*Klebsiella pneumoniae*] | *Klebsiella pneumoniae* |
| YP_005956056.1 | putative amino acid transport protein [*Klebsiella pneumoniae* KCTC 2242] | *Klebsiella pneumoniae* |
| WP_020803754.1 | inner membrane protein YgaZ [*Klebsiella pneumoniae*] | *Klebsiella pneumoniae* |
| WP_016161678.1 | inner membrane protein YgaZ [*Klebsiella* sp. KTE92] | *Klebsiella* sp. |
| WP_004174723.1 | membrane protein [*Klebsiella pneumoniae*] | *Klebsiella pneumoniae* |
| WP_004114705.1 | membrane protein [*Klebsiella oxytoca*] | *Klebsiella oxytoca* |
| YP_007990259.1 | ygaZ [*Klebsiella pneumoniae*] | *Klebsiella pneumoniae* |
| WP_004104780.1 | membrane protein [*Klebsiella oxytoca*] | *Klebsiella oxytoca* |
| WP_007370573.1 | membrane protein [*Kosakonia radicincitans*] | *Kosakonia radicincitans* |

TABLE 1-continued

YgaZ homologous proteins

| Acession Number | Name | *Organism* |
|---|---|---|
| WP_007370573.1 | membrane protein [*Kosakonia radicincitans*] | *Kosakonia radicincitans* |
| NP_668256.1 | hypothetical protein y0925 [*Yersinia pestis* KIM10+] | *Yersinia pestis* |
| WP_005119769.1 | branched-chain amino acid permease [*Shigella flexneri*] | *Shigella flexneri* |
| YP_069400.1 | LIV-E family branched chain amino acid exporter large subunit [*Yersinia pseudotuberculosis* IP 32953] | *Yersinia pseudotuberculosis* |
| WP_017893772.1 | membrane protein [*Serratia* sp. S4] | *Serratia* sp. |
| YP_001479963.1 | AzlC family protein [*Serratia proteamaculans* 568] | *Serratia proteamaculans* |
| WP_005189088.1 | membrane protein [*Yersinia intermedia*] | *Yersinia intermedia* |
| YP_004297214.1 | putative amino acid transporter [*Yersinia enterocolitica* subsp. *palearctica* 105.5R(r)] | *Yersinia enterocolitica* subsp. *Palearctica* |
| WP_019081387.1 | membrane protein [*Yersinia enterocolitica*] | *Yersinia enterocolitica* |
| WP_004392936.1 | membrane protein [*Yersinia kristensenii*] | *Yersinia kristensenii* |
| WP_016929851.1 | membrane protein [*Serratia marcescens*] | *Serratia marcescens* |
| WP_019845222.1 | membrane protein [*Dickeya zeae*] | *Dickeya zeae* |
| YP_003334823.1 | AzlC family protein [*Dickeya dadantii* Ech586] | *Dickeya dadantii* |
| YP_003042011.1 | conserved hypothetical protein [*Photorhabdus asymbiotica*] | *Photorhabdus asymbiotica* |
| WP_016941678.1 | membrane protein [*Dickeya zeae*] | *Dickeya zeae* |
| WP_005274999.1 | membrane protein [*Yersinia bercovieri*] | *Yersinia bercovieri* |
| CAC44347.1 | YgaZ protein [*Erwinia chrysanthemi*] | *Erwinia chrysanthemi* |
| WP_004704053.1 | membrane protein [*Yersinia aldovae*] | *Yersinia aldovae* |
| YP_003003219.1 | AzlC family protein [*Dickeya zeae* Ech1591] | *Dickeya zeae* |
| WP_004707388.1 | membrane protein [*Yersinia frederiksenii*] | *Yersinia frederiksenii* |
| WP_008812528.1 | membrane protein [*Enterobacteriaceae bacterium* 9_2_54FAA] | *Enterobacteriaceae bacterium* |
| YP_008231812.1 | membrane protein [*Serratia liquefaciens* ATCC 27592] | *Serratia liquefaciens* |
| YP_051597.1 | amino acid transporter [*Pectobacterium atrosepticum* SCRI1043] | *Pectobacterium atrosepticum* |
| WP_019455591.1 | membrane protein [*Serratia marcescens*] | *Serratia marcescens* |
| YP_007407667.1 AGE19648.1 NC_020211.1. | putative amino acid transporter YgaZ [*Serratia marcescens* WW4] | *Serratia marcescens* |
| WP_004716726.1 | membrane protein [*Yersinia rohdei*] | *Yersinia rohdei* |
| YP_003018879.1 | AzlC family protein [*Pectobacterium carotovorum* subsp. *carotovorum* PC1] | *Pectobacterium carotovorum* subsp. *Carotovorum* |
| WP_004873538.1 | membrane protein [*Yersinia mollaretii*] | *Yersinia mollaretii* |
| WP_005975645.1 | membrane protein [*Pectobacterium wasabiae*] | *Pectobacterium wasabiae* |
| YP_003260827.1 | AzlC family protein [*Pectobacterium wasabiae* WPP163] | *Pectobacterium wasabiae* |
| YP_002986523.1 | AzlC family protein [*Dickeya dadantii* Ech703] | *Dickeya dadantii* |
| YP_007345875.1 AGB83690.1 | putative branched-chain amino acid permease (azaleucine resistance) [*Serratia marcescens* FGI94] | *Serratia marcescens* |
| YP_004211503.1 | AzlC family protein [*Rahnella* sp. Y9602] | *Rahnella* sp. |
| YP_005400523.1 | AzlC family protein [*Rahnella aquatilis* HX2] | *Rahnella aquatilis* |
| WP_010305354.1 | membrane protein [*Pectobacterium carotovorum*] | *Pectobacterium carotovorum* |
| WP_010848732.1 | conserved hypothetical protein [*Xenorhabdus nematophila*] | *Xenorhabdus nematophila* |
| YP_003711585.1 CBJ89380.1 | hypothetical protein XNC1_1315 [*Xenorhabdus nematophila* ATCC 19061] | *Xenorhabdus nematophila* |
| YP_006500218.1 AFN33798.1 | hypothetical protein A225_4537 [*Klebsiella oxytoca* E718] | *Klebsiella oxytoca* |
| EHT06520.1 | inner membrane protein YgaZ [*Klebsiella oxytoca* 10-5246] | *Klebsiella oxytoca* |
| EKP29343.1 | AzlC family protein [*Klebsiella oxytoca* M5aI] | *Klebsiella oxytoca* |
| EJK15416.1 | putative amino acid transport protein [*Klebsiella pneumoniae* subsp. *pneumoniae* KPNIH18] | *Klebsiella pneumoniae* subsp. *Pneumoniae* |
| YP_006500218.1 | hypothetical protein A225_4537 [*Klebsiella oxytoca* E718] | *Klebsiella oxytoca* |
| YP_002920871.1 | putative amino acid transport protein [*Klebsiella pneumoniae* subsp. *pneumoniae* NTUH-K2044] | *Klebsiella pneumoniae* subsp. *Pneumoniae* |
| YP_003437997.1 | AzlC family protein [*Klebsiella variicola* At-22] | *Klebsiella variicola* |
| YP_003260827.1 | AzlC family protein [*Pectobacterium wasabiae* WPP163] | *Pectobacterium wasabiae* |
| WP_010305354.1 | membrane protein [*Pectobacterium carotovorum*] | *Pectobacterium carotovorum* |

TABLE 1-continued

| YgaZ homologous proteins | | |
|---|---|---|
| Acession Number | Name | *Organism* |
| YP_404404.1<br>ABB62913.1 | hypothetical protein SDY_2877 [*Shigella dysenteriae* Sd197] | *Shigella dysenteriae* |
| YP_311671.1.<br>NC_007384.1.<br>AAZ89436.1 | hypothetical protein SSON_2826 [*Shigella sonnei* Ss046] | *Shigella sonnei* |

TABLE 2

| YgaH homologous proteins | | |
|---|---|---|
| Acession Number | Name | Organism |
| YP_001455540.1<br>ABV15104.1 | hypothetical protein CKO_04032 [*Citrobacter koseri* ATCC BAA-895] | *Citrobacter koseri* |
| WP_005122930.1<br>EIQ78634.1 | branched-chain amino acid ABC transporter permease [*Shigella flexneri*] | *Shigella flexneri* |
| YP_007877062.1<br>AGJ89510.1 | L-valine exporter [*Raoultella ornithinolytica* B6] | *Raoultella ornithinolytica* |
| YP_008107734.1<br>WP_020454910.1<br>AGN85394.1 | branched-chain amino acid ABC transporter permease [*Enterobacter* sp. R4-368] | *Enterobacter* sp. |
| WP_004959351.1<br>EFE95944.1 | branched-chain amino acid ABC transporter permease [*Serratia odorifera*] | *Serratia odorifera* |
| YP_003884335.1<br>ADM99778.1 | hypothetical protein Dda3937_00895 [*Dickeya dadantii* 3937] | *Dickeya dadantii* |
| YP_006647985.1<br>AFR04732.1 | hypothetical protein PCC21_033290 [*Pectobacterium carotovorum* subsp. *carotovorum* PCC21] | *Pectobacterium carotovorum* subsp. *carotovorum* |
| YP_001007413.1<br>CAL13269.1 | hypothetical protein YE3239 [*Yersinia enterocolitica* subsp. *enterocolitica* 8081] | *Yersinia enterocolitica* subsp. *enterocolitica* |
| NP_928589.1<br>CAE13572.1 | hypothetical protein plu1278 [*Photorhabdus luminescens* subsp. *laumondii* TTO1] | *Photorhabdus luminescens* subsp. *laumondii* |
| WP_004847362.1<br>EHM42582.1 | branched-chain amino acid ABC transporter permease [*Hafnia alvei*] | *Hafnia alvei* |
| WP_016154157.1<br>EOQ28427.1<br>EOQ47452.1 | L-valine exporter [*Citrobacter* sp. KTE32] | *Citrobacter* sp. |
| WP_006687198.1<br>EFE06903.1 | branched-chain amino acid ABC transporter permease [*Citrobacter youngae*] | *Citrobacter youngae* |
| YP_005198837.1<br>AEX50697.1 | Branched-chain amino acid transport protein AzlD [*Rahnella aquatilis* CIP 78.65 = ATCC 33071] | *Rahnella aquatilis* |
| WP_009111643.1<br>EHD20335.1. | branched-chain amino acid ABC transporter permease [*Brenneria* sp. EniD312] | *Brenneria* sp. EniD312 |
| YP_003469115.1<br>CBJ82351.1 | transporter [*Xenorhabdus bovienii* SS-2004] | *Xenorhabdus bovienii* |
| NP_708496.1 | L-valine exporter [*Shigella flexneri* 2a str. 301] | *Shigella flexneri* |
| YP_409183.1.<br>NC_007613.1.<br>ABB67355.1. | conserved hypothetical protein [*Shigella boydii* Sb227] | *Shigella boydii* |
| WP_000119765.1 | branched-chain amino acid ABC transporter permease [*Shigella flexneri*] | *Shigella flexneri* |
| WP_003825969.1 | branched-chain amino acid ABC transporter permease [*Citrobacter* sp. 30_2] | *Citrobacter* sp. |
| WP_003037297.1 | branched-chain amino acid ABC transporter permease [*Citrobacter freundii*] | *Citrobacter freundii* |
| WP_003037297.1 | branched-chain amino acid ABC transporter permease [*Citrobacter freundii*] | *Citrobacter freundii* |
| EKU35015 | liv-e family branched chain amino acid small subunit [*Citrobacter* sp. L17] | *Citrobacter* sp. |
| WP_009652550.1 | branched-chain amino acid ABC transporter permease [*Klebsiella* sp. OBRC7] | *Klebsiella* sp. |
| WP_004853462.1 | branched-chain amino acid ABC transporter permease [*Klebsiella oxytoca*] | *Klebsiella oxytoca* |
| YP_005016080.1 | putative L-valine exporter [*Klebsiella oxytoca* KCTC 1686] | *Klebsiella oxytoca* |
| WP_017459326.1 | branched-chain amino acid ABC transporter permease [*Enterobacter cloacae*] | *Enterobacter cloacae* |
| WP_004205699.1 | L-valine exporter [*Klebsiella pneumoniae*] | *Klebsiella pneumoniae* |
| WP_004123982.1 | branched-chain amino acid ABC transporter permease [*Klebsiella oxytoca*] | *Klebsiella oxytoca* |
| WP_004132928.1 | L-valine exporter [*Klebsiella oxytoca*] | *Klebsiella oxytoca* |

TABLE 2-continued

| YgaH homologous proteins | | |
|---|---|---|
| Acession Number | Name | Organism |
| YP_002236979.1 | hypothetical protein KPK_1115 [*Klebsiella pneumoniae* 342] | *Klebsiella pneumoniae* |
| YP_005228385.1 | hypothetical protein KPHS_40850 [*Klebsiella pneumoniae* subsp. *pneumoniae* HS11286] | *Klebsiella pneumoniae* subsp. *Pneumoniae* |
| YP_001336648.1 | hypothetical protein KPN_03012 [*Klebsiella pneumoniae* subsp. *pneumoniae* MGH 78578] | *Klebsiella pneumoniae* subsp. *Pneumoniae* |
| YP_005956057.1. NC_017540.1. | putative L-valine exporter [*Klebsiella pneumoniae* KCTC 2242] | *Klebsiella pneumoniae* |
| WP_020803764.1 | hypothetical protein [*Klebsiella pneumoniae*] | *Klebsiella pneumoniae* |
| WP_004114708.1 | branched-chain amino acid ABC transporter permease [*Klebsiella oxytoca*] | *Klebsiella oxytoca* |
| WP_004104783.1 | branched-chain amino acid ABC transporter permease [*Klebsiella oxytoca*] | *Klebsiella oxytoca* |
| WP_007370572.1 EJI92176.1 | branched-chain amino acid transport family protein [*Kosakonia radicincitans*] | *Kosakonia radicincitans* |
| EJI93105.1 | branched-chain amino acid transport family protein [*Enterobacter radicincitans* DSM 16656] | *Enterobacter radicincitans* |
| NP_668255.1 | hypothetical protein y0924 [*Yersinia pestis* KIM10+] | *Yersinia pestis* |
| YP_069399.1 | hypothetical protein YPTB0858 [*Yersinia pseudotuberculosis* IP 32953] | *Yersinia pseudotuberculosis* |
| YP_001479964.1 | hypothetical protein Spro_3740 [*Serratia proteamaculans* 568] | *Serratia proteamaculans* |
| WP_005189085.1 | branched-chain amino acid ABC transporter permease [*Yersinia intermedia*] | *Yersinia intermedia* |
| YP_004297213.1 | hypothetical protein YE105_C1014 [*Yersinia enterocolitica* subsp. *palearctica* 105.5R(r)] | *Yersinia enterocolitica* subsp. *Palearctica* |
| WP_019081388.1 | branched-chain amino acid ABC transporter permease [*Yersinia enterocolitica*] | *Yersinia enterocolitica* |
| WP_004392937.1 | branched-chain amino acid ABC transporter permease [*Yersinia kristensenii*] | *Yersinia kristensenii* |
| WP_016929852.1 | branched-chain amino acid ABC transporter permease [*Serratia marcescens*] | *Serratia marcescens* |
| WP_019845221.1 | branched-chain amino acid ABC transporter permease [*Dickeya zeae*] | *Dickeya zeae* |
| YP_003334824.1 | hypothetical protein Dd586_3285 [*Dickeya dadantii* Ech586] | *Dickeya dadantii* |
| YP_003042012.1. NC_012962.1. | conserved hypothetical protein [*Photorhabdus asymbiotica*] | *Photorhabdus asymbiotica* |
| WP_016941677.1 | branched-chain amino acid ABC transporter permease [*Dickeya zeae*] | *Dickeya zeae* |
| WP_005275000.1 | branched-chain amino acid ABC transporter permease [*Yersinia bercovieri*] | *Yersinia bercovieri* |
| CAC44348.1 | YgaH protein [*Erwinia chrysanthemi*] | *Erwinia chrysanthemi* |
| WP_004704054.1 | branched-chain amino acid ABC transporter permease [*Yersinia aldovae*] | *Yersinia aldovae* |
| YP_003003218.1 | hypothetical protein Dd1591_0860 [*Dickeya zeae* Ech1591] | *Dickeya zeae* Ech1591 |
| WP_004707387.1 | branched-chain amino acid ABC transporter permease [*Yersinia frederiksenii*] | *Yersinia frederiksenii* |
| WP_008812527.1 | branched-chain amino acid ABC transporter permease [*Enterobacteriaceae bacterium* 9_2_54FAA] | *Enterobacteriaceae bacterium* |
| YP_008231813.1 | branched-chain amino acid ABC transporter permease [*Serratia liquefaciens* ATCC 27592] | *Serratia liquefaciens* |
| YP_051598.1 | hypothetical protein ECA3510 [*Pectobacterium atrosepticum* SCRI1043] | *Pectobacterium atrosepticum* |
| WP_019455592.1 | branched-chain amino acid ABC transporter permease [*Serratia marcescens*] | *Serratia marcescens* |
| YP_007407668.1 | putative amino acid transporter YgaH [*Serratia marcescens* WW4] | *Serratia marcescens* |
| WP_004716724.1 | branched-chain amino acid ABC transporter permease [*Yersinia rohdei*] | *Yersinia rohdei* |
| YP_003018880.1. NC_012917.1. | hypothetical protein PC1_3328 [*Pectobacterium carotovorum* subsp. *carotovorum* PC1] | *Pectobacterium carotovorum* subsp. *Carotovorum* |
| WP_004873539.1 | branched-chain amino acid ABC transporter permease [*Yersinia mollaretii*] | *Yersinia mollaretii* |
| WP_005975643.1 | branched-chain amino acid ABC transporter permease [*Pectobacterium wasabiae*] | *Pectobacterium wasabiae* |
| YP_003260828.1 | hypothetical protein Pecwa_3484 [*Pectobacterium wasabiae* WPP163] | *Pectobacterium wasabiae* |
| YP_002986522.1 | hypothetical protein Dd703_0892 [*Dickeya dadantii* Ech703] | *Dickeya dadantii* |
| YP_007345876.1 | Branched-chain amino acid transport protein (AzID) [*Serratia marcescens* FGI94] | *Serratia marcescens* |

TABLE 2-continued

| YgaH homologous proteins | | |
|---|---|---|
| Acession Number | Name | Organism |
| YP_004211502.1 | branched-chain amino acid transport [*Rahnella* sp. Y9602] | *Rahnella* sp. |
| YP_005400522.1 NC_017047.1. | putative L-valine exporter [*Rahnella aquatilis* HX2] | *Rahnella aquatilis* |
| WP_010305358.1 | branched-chain amino acid ABC transporter permease [*Pectobacterium carotovorum*] | *Pectobacterium carotovorum* |
| YP_003711584.1. NC_014228.1. | hypothetical protein XNC1_1314 [*Xenorhabdus nematophila* ATCC 19061] | *Xenorhabdus nematophila* |
| YP_006500219.1 AFN29790.1 | branched-chain amino acid transport [*Klebsiella oxytoca* E718] | *Klebsiella oxytoca* |
| EHT06521.1 | hypothetical protein HMPREF9690_03780 [*Klebsiella oxytoca* 10-5246] | *Klebsiella oxytoca* |
| EKP29342.1. | L-valine exporter [*Klebsiella oxytoca* M5al] | *Klebsiella oxytoca* |
| EJK15417.1. | putative L-valine exporter [*Klebsiella pneumoniae* subsp. *pneumoniae* KPNIH18] | *Klebsiella pneumoniae* subsp. *Pneumoniae* |
| YP_006500219.1 | branched-chain amino acid transport [*Klebsiella oxytoca* E718] | *Klebsiella oxytoca* |
| BAH64805.1. | hypothetical protein KP1_4275 [*Klebsiella pneumoniae* subsp. *pneumoniae* NTUH-K2044]-ygaH | *Klebsiella pneumoniae* subsp. *Pneumoniae* |
| YP_003437996.1 | hypothetical protein Kvar_1056 [*Klebsiella variicola* At-22] | *Klebsiella variicola* |
| YP_003260828.1 | hypothetical protein Pecwa_3484 [*Pectobacterium wasabiae* WPP163] | *Pectobacterium wasabiae* |
| WP_010282658.1 | branched-chain amino acid ABC transporter permease [*Pectobacterium carotovorum*] | *Pectobacterium carotovorum* |
| YP_404405.1. NC_007606.1. ABB62914.1. | hypothetical protein SDY_2878 [*Shigella dysenteriae* Sd197] | *Shigella dysenteriae* |
| WP_000119748.1 | branched-chain amino acid ABC transporter permease [*Shigella dysenteriae*] | *Shigella dysenteriae* |
| YP_311672.1 AAZ89437.1 | hypothetical protein SSON_2827 [*Shigella sonnei* Ss046] | *Shigella sonnei* |
| WP_005150562.1 | putative membrane protein [*Shigella sonnei*] | *Shigella sonnei* |
| WP_000119744.1 | branched-chain amino acid ABC transporter permease [*Shigella boydii*] | *Shigella boydii* |
| WP_002427075.1 | branched-chain amino acid ABC transporter permease [*Yersinia pestis*] | *Yersinia pestis* |
| WP_017491438.1 | branched-chain amino acid ABC transporter permease [gamma proteobacterium WG36] | gamma *proteobacterium* |
| WP_002366138.1 | branched-chain amino acid transport family protein, partial [*Yersinia pestis*] | *Yersinia pestis* |

With accession number disclosed in the tables for each homolog the man skilled in the art is able to obtain the amino acid sequence and its nucleotidic coding sequence on NCBI databases for instance.

From the amino acid sequence or nucleotidic sequence, it is a routine task for the man skilled in the art to obtain genes encoding these homologues. It can be done either by artificial synthesis of the gene coding the protein of interest from its amino acid sequence or by PCR amplification of the coding region of interest from the corresponding genomic DNA. In the context of the invention, these genes are called "ygaZ or ygaH homologous genes". The sequences of these ygaZH homologous genes may be adjusted to the codon bias of the host microorganism.

In a specific embodiment of the invention, the recombinant microorganism overexpresses the genes ygaZ and ygaH coding the proteins whose sequences are respectively disclosed in SEQ ID NO: 1 and SEQ ID NO: 2 or their homologous genes. Preferably, ygaZ and ygaH homologous genes are composed by the gene pair originating from the same organism and composed by the homologous gene of ygaZ and the homologous gene of ygaH. However mismatch pair of an ygaZ homologous gene from a first organism and an ygaH homologous gene from a second organism could be used.

YgaZH homologous genes are chosen among genes encoding the YgaZ and YgaH homologues disclosed respectively in table 1 and in table 2. Preferably, ygaZH homologous genes are chosen among genes encoding YgaZH homologues from *Citrobacter* species, *Shigella* species, *Raoultella* species, *Enterobacter* species, *Yersinia* species and *Photorhabdus* species. More preferably ygaZH homologous genes originate from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii*. Most preferably, ygaZH homologous genes originate from *Citrobacter koseri, Citrobacter youngae, Citrobacter freundii* or *Enterobacter* sp.

Therefore, ygaZH homologous genes are preferably chosen among genes coding the pair of YgaZ homologue and YgaH homologue defined respectively by: SEQ ID NO: 3 and SEQ ID NO: 4 from *Citrobacter koseri*, SEQ ID NO: 5 and SEQ ID NO: 6 from *Shigella flexneri*, SEQ ID NO: 7 and SEQ ID NO: 8 from *Raoultella ornithinolytica*, SEQ ID NO: 9 and SEQ ID NO: 10 from *Enterobacter* sp. (R4-368), SEQ ID NO: 11 or 12 and SEQ ID NO: 13 or 14 from *Yersinia enterocolitica* subsp. *enterocolitica*, SEQ ID NO: 15 and SEQ ID NO: 16 from *Photorhabdus luminescens* subsp. *laumondii*, SEQ ID NO: 17 and SEQ ID NO: 18 from *Citrobacter youngae*, SEQ ID NO: 19 and SEQ ID NO: 20 from *Citrobacter freundii.*

In a specific embodiment, the recombinant microorganism is characterized by:

attenuation of at least one of the gene metN, metI or metQ; and overexpression of the genes ygaZH or their homologous genes originating from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii.*

In another specific embodiment, the recombinant microorganism is characterized by:

attenuation of the gene metN; and overexpression of the genes ygaZH or their homologous genes *Citrobacter koseri, Shigella flexneri, Raoultella ornithinolytica, Enterobacter* sp., *Yersinia enterocolitica, Photorhabdus luminescens, Citrobacter youngae* or *Citrobacter freundii.*

In another specific embodiment, the recombinant microorganism is characterized by:

attenuation of the gene metI; and overexpression of the genes ygaZH or their homologous genes *Citrobacter koseri, Shigella flexneri, Raoultella ornithinolytica, Enterobacter* sp., *Yersinia enterocolitica, Photorhabdus luminescens, Citrobacter youngae* or *Citrobacter freundii.*

In another specific embodiment, the recombinant microorganism is characterized by:

attenuation of the gene metQ; and overexpression of the genes ygaZH or their homologous genes *Citrobacter koseri, Shigella flexneri, Raoultella ornithinolytica, Enterobacter* sp., *Yersinia enterocolitica, Photorhabdus luminescens, Citrobacter youngae* or *Citrobacter freundii.*

In another specific embodiment, the recombinant microorganism is characterized by:

attenuation of the genes metN, metI and metQ; and overexpression of the genes ygaZH or their homologous genes *Citrobacter koseri, Shigella flexneri, Raoultella ornithinolytica, Enterobacter* sp., *Yersinia enterocolitica, Photorhabdus luminescens, Citrobacter youngae* or *Citrobacter freundii.*

In a preferred embodiment of the invention, these genes are overexpressed under the control of an inducible promoter. The man skilled in the art knows such inducible promoters. For instance, promoters like $\lambda P_R$ or $\lambda P_L$ may be used to overexpress ygaZH genes or ygaZH homologous genes originating from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii* in the recombinant microorganism of the invention.

It is another object of the invention to identify ygaZH homologous genes and to overexpress said genes in amino-acid producer microorganism, alone or in combination with other genetic modifications as disclosed below.

Optimisation of Methionine Biosynthesis Pathway

The recombinant microorganism according to the invention is modified for improving the production of methionine. Genes involved in methionine production are well known in the art, and comprise genes involved in the methionine specific biosynthesis pathway as well as genes involved in precursor-providing pathways and genes involved in methionine consuming pathways.

Efficient production of methionine requires the optimisation of the methionine specific pathway and several precursor—providing pathways. Methionine producing strains have already been described, in particular in patent applications WO 2005/111202, WO 2007/077041 and WO 2009/043803. These applications are incorporated as reference into this application.

Except otherwise stated, all the genes mentioned below concerning optimisation of methionine biosynthesis pathway are referring to those from *E. coli.*

In a specific embodiment of the invention, the recombinant microorganism is modified as described below: the expression of at least one gene chosen among ptsG, pyc, pntAB, cysP, cysU, cysW, cysA, cysM, cysJ, cysI, cysH, gcvT, gcvH, gcvP, lpd, serA, serB, serC, cysE, metF, metH, fldA, fpr, metA, metA* allele encoding for an enzyme with reduced feed-back sensitivity to S-adenosylmethionine and/or methionine, thrA, and thrA* allele encoding for an enzyme with reduced feed-back inhibition to threonine is increased.

ptsG encodes the PTS enzyme $IICB^{Glc}$ as described in patent application WO 2013/001055.

pyc encodes a pyruvate carboxylase as described in patent application WO2013/001055. In a preferred embodiment, the pyc gene is heterologous and is chosen from pyc genes from *Rhizobium etli, Bacillus subtilis, Lactococcus lactis, Pseudomonas fluorescens* or *Corynebacterium* species, pntAB encode subunits of a membrane-bound transhydrogenase, such as described in patent application WO 2012/055798, cysP encodes a periplasmic sulphate binding protein, as described in WO 2007/077041 and in WO 2009/043803, cysU encodes a component of sulphate ABC transporter, as described in WO 2007/077041 and in WO 2009/043803, cysW encodes a membrane bound sulphate transport protein, as described in WO 2007/077041 and in WO 2009/043803, cysA encodes a sulphate permease, as described in WO 2007/077041 and in WO 2009/043803, cysM encodes an O-acetyl serine sulfhydralase, as described in WO 2007/077041 and in WO 2009/043803, cysI and cysJ encode respectively the alpha and beta subunits of a sulfite reductase as described in WO 2007/077041 and in WO 2009/043803. Preferably cyst and cysJ are overexpressed together, cysH encodes an adenylylsulfate reductase, as described in WO2007/077041 and in WO 2009/043803.

Increasing C1 metabolism is also a modification that leads to improved methionine production. It relates to the increase of the activity of at least one enzyme involved in the C1 metabolism chosen among GcvTHP, Lpd, MetF or MetH. In a preferred embodiment of the invention, the one carbon metabolism is increased by enhancing the expression and/or the activity of at least one of the following:

gcvT, gcvH, gcvP, and lpd, coding for the glycine cleavage complex, as described in patent application WO 2007/077041. The glycine-cleavage complex (GCV) is a multienzyme complex that catalyzes the oxidation of glycine, yielding carbon dioxide, ammonia, methylene-THF and a reduced pyridine nucleotide. The GCV complex consists of four protein components, the glycine dehydrogenase said P-protein (GcvP), the lipoyl-GcvH-protein said H-protein (GcvH), the aminomethyltransferase said T-protein (GcvT), and the dihydrolipoamide dehydrogenase said L-protein (GcvL or Lpd). P-protein catalyzes the pyridoxal phosphate-dependent liberation of CO2 from glycine, leaving a methylamine moiety. The methylamine moiety is transferred to the lipoic acid group of the H-protein, which is bound to the P-protein prior to decarboxylation of glycine. The T-protein catalyzes the release of NH3 from the methylamine group and transfers the remaining C1 unit to THF, forming methylene-THF. The L protein then oxidizes the lipoic acid component of the H-protein and transfers the electrons to $NAD^+$, forming NADH;

MetF encoding a methylenetetrahydrofolate reductase, as described in patent application WO 2007/077041;

MetH (B12-dependent homocysteine-N5-methyltetrahydrofo late transmethylase) encoding methyltransferases.

The overexpression of at least one of the following genes involved in serine biosynthesis also reduces the production of the by-product isoleucine:

serA which encodes a phosphoglycerate dehydrogenase, as described in WO 2007/077041 and in WO 2009/043803, serB which encodes a phosphoserine phosphatase, as described in WO 2007/077041 and in WO 2009/043803, serC which encodes a phosphoserine aminotransferase, as described in WO 2007/077041 and in WO 2009/043803.

The overexpression of the following genes has already been shown to improve the production of methionine:

cysE encodes a serine acyltransferase; its overexpression allows an increase in methionine production, as described in WO 2007/077041;

metA encodes a homoserine succinyltransferase. The allele metA* codes for an enzyme with reduced feed-back sensitivity to S-adenosylmethionine and/or methionine. Preferentially, the allele metA* described in the patent application WO 2005/111202 is used;

thrA encodes an aspartokinase/homoserine dehydrogenase; the thrA* allele codes for an enzyme with reduced feed-back inhibition to threonine, as described in WO 2005/111202.

In a specific embodiment of the invention, genes may be under control of an inducible promoter. In a preferred embodiment of the invention, at least one of these genes is under the control of a temperature inducible promoter. Preferably, the expression of at least one of the genes: thrA, cysE, metA, is under the control of an inducible promoter, directly or indirectly. More preferably, the genes thrA, cysE and metA are under control of an inducible promoter, directly or indirectly. In a preferred embodiment of the invention, expression of thrA gene is under direct control of an inducible promoter and expression of cysE gene is under polar effect of inducible expression of thrA gene. In another preferred embodiment of the invention, expression of thrA gene is under direct control of an inducible promoter and expressions of cysE and metA genes are under polar effect of inducible expression of thrA gene.

In a most preferred embodiment, the temperature inducible promoter belongs to the family of $P_R$ promoters. A methionine producing strain having genes under control of inducible promoters is described in patent application WO 2011/073122.

In another specific embodiment of the invention, the microorganism has been further modified, and the expression of at least one of the following genes is attenuated: metJ, pykA, pykF, purU, ybdL, yncA, metE, dgsA or udhA.

the gene metJ codes for the repressor protein MetJ (GenBank 1790373), responsible for the down-regulation of the methionine regulon as was suggested in patent application JP 2000/157267, The genes pykA and pykF code for the enzymes 'pyruvate kinase'. The attenuation of the expression of at least one or both of the pyruvate kinases decrease the consumption of phosphoenol pyruvate (PEP). Increased availability of PEP can increase the production of oxaloacetate, an important precursor of aspartate, which in turn is a precursor of methionine, as described in WO 2007/077041 and in WO 2009/043803, purU codes for a formyltetrahydrofolate deformylase, an enzyme that catalyzes the formyl-THF deformylase reaction. The attenuation of the deformylase activity increases the production of methyl-THF that is required for methylation of homocysteine. Loss of C1 metabolites by deformylation leads to an increased production of homocysteine that cannot be transformed into methionine. Homocysteine can then be a substrate for the enzyme cystathionine gamma synthase (MetB) that can catalyze the reaction between 0-succinylhomoserine and homocysteine resulting in the production of homolanthionine, as described in WO 2007/077041 and in WO 2009/043803, ybdL encodes an aminotransferase as described in patent application WO 2012/090021, yncA encodes a N-acyltransferase, as described in patent application WO 2010/020681, metE encodes a cobalamin-independent methionine synthase, as described in patent application PCT/IB2012/001336, dgsA, better known as Mlc, encodes a transcriptional dual regulator that controls the expression of genes encoding enzymes of the phosphotransferase (PTS) and phosphoenolpyruvate (PEP) systems as described in patent application WO 2013/001055, udhA encodes soluble pyridine nucleotide transhydrogenase, as described in patent application WO 2012/055798.

In a more preferred embodiment of the invention, the fermentative production of methionine and/or its derivatives by a recombinant microorganism, wherein the methionine import is attenuated and the methionine efflux is enhanced, from glucose as a main carbon source, may be achieved through a combination of the above discussed modifications in said microorganism, for example:

the expression of the gene metJ is attenuated and the expression of a metA* allele encoding for an enzyme with reduced feed-back sensitivity to S-adenosylmethionine and/or methionine (MetA*) is enhanced;

the expression of the gene metJ is attenuated; the expression of a metA* allele encoding for an enzyme with reduced feed-back sensitivity to S-adenosylmethionine and/or methionine (MetA*) is enhanced; and the expression of a thrA* allele encoding for an enzyme with reduced feed-back inhibition to threonine (thrA*) is enhanced;

the expression of the gene metJ is attenuated; the expression of a metA* allele encoding for an enzyme with reduced feed-back sensitivity to S-adenosylmethionine and/or methionine (MetA*) is enhanced; the expression of a thrA* allele encoding for an enzyme with reduced feed-back inhibition to threonine (thrA*) is enhanced; and the expression of the gene cysE is enhanced;

the expression of the gene metJ is attenuated; the expression of a metA* allele encoding for an enzyme with reduced feed-back sensitivity to S-adenosylmethionine and/or methionine (MetA*) is enhanced; the expression of a thrA* allele encoding for an enzyme with reduced feed-back inhibition to threonine (thrA*) is enhanced; the expression of the gene cysE is enhanced; and the expression of the genes metF and/or metH is enhanced.

In a particular aspect of the invention, the recombinant microorganism comprises the following genetic modifications:

the genes metN, metI, metQ are deleted and the genes ygaZ and ygaH or their homologous genes originating from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii* are overexpressed, the expression of the genes metA*, metH, cysPUWAM, cysJIH, gcvTHP, metF, serA, serB, serC, cysE, thrA*, ptsG and pyc are enhanced, and the expression of the genes metJ, pykA, pykF, purU, metE, dgsA and yncA are attenuated.

In a particular embodiment of the invention, the microorganism is from the bacterial family Enterobacteriaceae or Corynebacteriaceae.

Preferentially, the microorganism is *Escherichia coli* or *Corynebacterium glutamicum*. More preferentially the microorganism of the invention is *E. coli.*

Culture Conditions

In a second aspect of the invention, a method is optimised for the fermentative production of methionine and/or its derivatives. It comprises the followings steps:

Culturing a recombinant microorganism wherein the methionine import is attenuated by attenuating the expression of at least one gene among metN, metI, metQ and the methionine efflux is enhanced by overexpressing the genes ygaZH or their homologous genes in an appropriate culture medium comprising a fermentable source of carbon and a source of sulphur, and, Recovering methionine and/or its derivatives from the culture medium.

Those skilled in the art are able to define the culture conditions for the microorganisms according to the invention. In particular the bacteria are fermented at a temperature between 20° C. and 55° C., preferentially between 25° C. and 40° C., and more specifically about 30° C. for *C. glutamicum* and about 37° C. for *E. coli.*

For *E. coli*, the culture medium can be of identical or similar composition to an M9 medium (Anderson, 1946), an M63 medium (Miller, 1992); or a medium such as defined by Schaefer et al., (1999).

For *C. glutamicum*, the culture medium can be of identical or similar composition to BMCG medium (Liebl et al., 1989) or to a medium such as described by Riedel et al., (2001).

In the method of the invention, the ygaZH homologous genes which are overexpressed in the recombinant microorganism are preferably chosen among the group consisting in homologous genes from *Citrobacter* species, *Shigella* species, *Raoultella* species, *Enterobacter* species, *Yersinia* species and *Photorhabdus* species, and more preferably originate from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii.*

According to a specific aspect of the invention, the method is performed with a recombinant microorganism that comprises:

a. deletion of at least one gene chosen among metN, metI or metQ, and b. overexpression of the genes ygaZH or their homologous genes.

In this specific aspect of the method of the invention, said ygaZH homologous genes are preferably chosen among the group consisting in homologous genes from *Citrobacter* species, *Shigella* species, *Raoultella* species, *Enterobacter* species, *Yersinia* species and *Photorhabdus* species, and more preferably chosen among the groups consisting in homologous genes from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii.*

In the method of the invention, the ygaZH homologous genes which are overexpressed in the recombinant microorganism are most preferably originating from *Citrobacter koseri, Citrobacter youngae, Citrobacter freundii* or *Enterobacter* sp.

In some embodiment of the invention, the growth of the recombinant microorganism is subjected to a limitation or starvation for one or several inorganic substrate, in particular phosphate and/or potassium, in the culture medium. It refers to condition under which growth of the microorganisms is governed by the quantity of an inorganic chemical supplied that still permits weak growth. Such limitation in microorganism growth has been described in the patent application WO 2009/043372. In a preferred embodiment of the invention, the culture is subjected to phosphate limitation. In a particular embodiment of the method of the invention, the recombinant microorganism is from the bacterial family Enterobacteriaceae or Corynebacteriaceae. Preferentially, the recombinant microorganism is *Escherichia coli* or *Corynebacterium glutamicum*, and more preferentially the recombinant microorganism of the invention is *E. coli.*

The action of "recovering methionine and/or its derivatives from the culture medium" designates the action of recovering L-methionine and/or one of its derivatives, in particular N-acetyl methionine (NAM) and S-adenosyl methionine (SAM) and all other derivatives that may be useful such as hydroxy-methionine (or methionine hydroxy analogue or MHA). The methods for the recovery and purification of the produced compounds are well known to those skilled in the art (see in particular WO 2005/007862, WO 2005/059155). Preferably, the step of recovering methionine and/or its derivatives comprises a step of concentration of methionine and/or its derivatives in the fermentation broth.

The amount of product in the fermentation medium can be determined using a number of methods known in the art, for example, high performance liquid chromatography (HPLC) or gas chromatography (GC). For example the quantity of methionine obtained in the medium is measured by HPLC after OPA/Fmoc derivatization using L-methionine (Fluka, Ref 64319) as a standard. The amount of NAM is determinated using refractometric HPLC using NAM (Sigma, Ref 01310) as a standard.

EXAMPLES

The present invention is further defined in the following examples. It should be understood that these examples, while indicating preferred embodiments of the invention, are given by way of illustration only. From above disclosure and these examples, the man skilled in the art can make various changes of the invention to adapt it to various uses and conditions without modify the essentials means of the invention.

In particular, examples show modified *Escherichia coli* (*E. coli*) strains, but these modifications can easily be performed in other microorganisms of the same family.

*Escherichia coli* belongs to the Enterobacteriaceae family, which comprises members that are Gram-negative, rod-shaped, non-spore forming and are typically 1-5 μm in length. Most members have flagella used to move about, but a few genera are non-motile. Many members of this family are a normal part of the gut flora found in the intestines of humans and other animals, while others are found in water or soil, or are parasites on a variety of different animals and plants. *E. coli* is one of the most important model organisms, but other important members of the Enterobacteriaceae family include *Klebsiella*, in particular *Klebsiella terrigena, Klebsiella planticola* or *Klebsiella oxytoca*, and *Salmonella*.

Moreover, several patent applications point out that optimisation for methionine production can easily be applied in *E. coli* and in *Corynebacterium glutamicum* without undue experimentation.

Protocols

Several protocols have been used to construct methionine producing strains described in the following examples.

Protocol 1 (Chromosomal modifications by homologous recombination and selection of recombinants) and protocol 2 (Transduction of phage P1) used in this invention have been fully described in patent application WO 2013/001055.

Protocol 3: Construction of Recombinant Plasmids

Recombinant DNA technology is well described and known by the man skilled in the art. Briefly, the DNA fragments were PCR amplified using oligonucleotides (that the person skilled in the art will be able to define) and MG1655 genomic DNA as matrix. The DNA fragments and chosen plasmid were digested with compatible restriction enzyme (that the person skilled in the art is able to define), then ligated and transformed in competent cells. Transformants were analysed and recombinant plasmid of interest were verified by DNA sequencing.

TABLE 3 oligonucleotides sequences cited in the following examples

| SEQ ID NO | Sequence 5' → 3' |
|---|---|
| 21 | ATGATAAAACTTTCGAATATCACCAAAGTGTTCCACC AGGGCACCCGCACCATCCAGGCGTTGAACAACGTCAG CCTGCATGTAGGCTGGAGCTGCTTCG |
| 22 | TACCAGCCTTTAACAGCTCCGCCGTTAAACACTTTGT TTGCTGCTTCGTAAACTTCGTCAGACTGATAAGCCTG GACGAACATATGAATATCCTCCTTAG |

Protocol 4: Plasmid Curing

This plasmid curing method is based on the high-voltage electroporation which is usually used to transform DNA. For plasmid curing, the principle is rather the same except that no DNA is added to cell before the electric shock (Heery et al, 1989).

DNA transformation technologies are well described and known by the man skilled in the art.

Briefly, the strain for which the plasmid has to be removed was cultured until exponential growth phase. Then, the cells were pelleted and washed three times in sterile deionised water. The cells were incubated on ice for five to ten minutes before to go through one electric pulse at 2.50 kV, 25 μF (time constant approximate 4.5 ms). One mL of SOC buffer was added immediately after pulsing and the cells were grown at appropriate temperature for one to two hours before plating on non-selective media for plasmid to get rid (antibiotics are added according to the other plasmids to keep into the strain). After isolation of the cured cells, the absence of plasmid was verified.

Example 1

Overexpression of a L-Methionine Secretion System in a L-Methionine Overproducer *E. coli* Recombinant Strain—Construction of Strain 1

Methionine producing strains 16 described in patent application WO 2013/001055 (which is incorporated as reference into this application) was used as recipient strain. This strain contains the mutation in metE gene disclosed in patent application WO2013/190343.

The gene encoding the cobalamin-dependent methionine synthase, metH, was overproduced by using the same promoter and ribosome binding site as described in patent application WO 2007/077041 and a bacterial artificial chromosome (pCC1BAC, Epicentre). More precisely, metH gene and the artificial promoter were cloned into the pCC1BAC type plasmid contained in strain 17 described in patent application WO 2013/001055. This plasmid was named pME1109.

In parallel, genes fldA and fpr encoding for the reactivation system of MetH, were overexpressed from the moderate plasmid copy number pCL1920 (Lerner & Inouye, 1990) by using their natural promoters. This plasmid was named pME 1089.

Thirdly, the genes ygaZH encoding the exporter of methionine, were overexpressed. They were cloned on the moderate plasmid copy number pCL1920 (Lerner & Inouye, 1990) with the use of the natural promoter of ygaZ. More precisely, ygaZH operon and its promoter were cloned into the pME1089 described above. This plasmid was named pME1219.

Finally, the plasmids pME 1109 and pME1219 were transformed into the Methionine producing strain 16 of patent application WO 2013/001055, giving the strain 1.

Example 2

Deletion of the L-Methionine Uptake System in a L-Methionine Overproducer *E. coli* Strain—Construction of Strains 2, 3, 4 and 5

The methionine producing strain 16 of patent application WO2013/001055 was transformed with plasmids pME1109 and pME1089 (described in Example 1), giving the rise to strain 2.

To inactive the methionine importer encodes by the metNIQ operon in strain 2, the homologous recombination strategy described by Datsenko & Wanner, 2000 (according to Protocol 1) was used. Thus the oligonucleotides, Ome0233/Ome0232 (SEQ ID No 21 and 22 listed in table 1) were used to PCR amplified the chloramphenicol resistance cassette from the plasmid pKD3. The PCR product obtained was then introduced by electroporation into the strain MG1655 metA*11 (pKD46). The chloramphenicol resistant transformants were then selected and the insertion of the resistance cassette was verified by a PCR analysis with appropriate oligonucleotides. The strain retained is designated MG1655 metA*11 ΔmetNIQ::Cm. Finally, the ΔmetNIQ::Cm deletion was transferred by P1 phage transduction (according to Protocol 2) from the MG1655 metA*11 ΔmetNIQ::Cm strain to strain 2. Chloramphenicol resistant transductants were selected and the presence of ΔmetNIQ::Cm chromosomal deletion was verified by PCR with appropriate oligonucleotides. The strain retained was called strain 3.

As the same manner, the 3 genes, metN, metI and metQ were deleted in strain 1 described in patent application WO2013/001055. This strain 1 from patent application WO 2013/001055, is re-named herein as strain 4 to be the reference of strain 5. The deletion of metNIQ performed into strain 4 as described above, gave rise to strain 5.

Example 3

Combination of the Overexpression of a L-Methionine Secretion System with the Deletion of the L-Methionine Uptake System in a L-Methionine Overproducer *E. coli* Strain—Construction of Strain 6

To inactivate the methionine importer encodes by metNIQ operon in the strain overproducing the methionine exporter encodes by ygaZH operon, the ΔmetNIQ::Cm deletion was transferred by P1 phage transduction (according to Protocol 2) from the MG1655 metA*11 ΔmetNIQ::Cm strain to methionine producing strain 1. Chloramphenicol resistant transductants were selected and the presence of ΔmetNIQ::Cm chromosomal deletion was verified by PCR with appropriate oligonucleotides. The strain retained was called strain 6.

Example 4

Production of L-Methionine by Fermentation in Bio-Reactor

Strains that produced L-methionine were tested under production conditions in 2.5 L reactors (Pierre Guerin) using a fedbatch strategy.

Briefly, an 24 hours culture grown in 10 mL LB medium with 2.5 $g \cdot L^{-1}$ glucose was used to inoculate a 24 hours preculture in minimal medium (B1a). These incubations were carried out in 500 mL baffled flasks containing 50 mL of minimal medium (B1a) in a rotary shaker (200 RPM). The first preculture was realized at a temperature of 30° C., the second one at a temperature of 34° C.

A third preculture step was carried out in bio-reactors (Sixfors) filled with 200 mL of minimal medium (Bib) inoculated to a biomass concentration of 1.2 $g \cdot L^{-1}$ with 5 mL concentrated preculture. The preculture temperature was maintained constant at 34° C. and the pH was automatically adjusted to a value of 6.8 using a 10% $NH_4OH$ solution. The dissolved oxygen concentration was continuously adjusted to a value of 30% of the partial air pressure saturation with air supply and/or agitation. After glucose exhaustion from the batch medium, the fedbatch was started with an initial flow rate of 0.7 $mL \cdot h^{-1}$, before increasing exponentially for 26 hours with a growth rate of 0.13 If in order to obtain a final cellular concentration of about 20 $g \cdot L^{-1}$.

TABLE 4

Preculture batch mineral medium composition (B1a and B1b)

| Compound | B1a Concentration ($g \cdot L^{-1}$) | B1b Concentration ($g \cdot L^{-1}$) |
|---|---|---|
| $Zn(CH_3COO)_2 \cdot 2H_2O$ | 0.0130 | 0.0130 |
| $CuCl_2 \cdot 2H_2O$ | 0.0015 | 0.0015 |
| $MnCl_2 \cdot 4H_2O$ | 0.0150 | 0.0150 |
| $CoCl_2 \cdot 6H_2O$ | 0.0025 | 0.0025 |
| $H_3BO_3$ | 0.0030 | 0.0030 |
| $Na_2MoO_4 \cdot 2H_2O$ | 0.0025 | 0.0025 |
| Fe(III) citrate $H_2O$ | 0.1064 | 0.1064 |
| EDTA | 0.0084 | 0.0084 |
| $MgSO_4 \cdot 7H_2O$ | 1.00 | 1.00 |
| $CaCl_2 \cdot 2H_2O$ | 0.08 | 0.08 |
| Citric acid | 1.70 | 1.70 |
| $KH_2PO_4$ | 4.56 | 4.56 |
| $K_2HPO_4 \cdot 3H_2O$ | 2.53 | 2.53 |
| $(NH_4)_2HPO_4$ | 1.11 | 1.11 |
| $(NH_4)_2SO_4$ | 4.90 | 4.90 |
| $(NH_4)_2S_2O_3$ | 1.00 | 1.00 |
| Thiamine | 0.01 | 0.01 |
| Vitamin B12 | 0.01 | 0.01 |
| Glucose | 30.00 | 5.00 |
| MOPS | 30.00 | 0.00 |
| $NH_4OH$ 28% | Adjusted to pH 6.8 | Adjusted to pH 6.8 |

TABLE 5

Preculture fedbatch mineral medium composition (F1)

| Compound | Concentration ($g \cdot L^{-1}$) |
|---|---|
| $Zn(CH_3COO)_2 \cdot H_2O$ | 0.0104 |
| $CuCl_2 \cdot 2H_2O$ | 0.0012 |
| $MnCl_2 \cdot 4H_2O$ | 0.0120 |
| $CoCl_2 \cdot 6H_2O$ | 0.0020 |
| $H_3BO_3$ | 0.0024 |
| $Na_2MoO_4 \cdot 2H_2O$ | 0.0020 |
| Fe(III) citrate $H_2O$ | 0.0524 |
| EDTA | 0.0067 |
| $MgSO_4$ | 5.00 |
| $(NH_4)_2SO_4$ | 8.32 |
| $Na_2SO_4$ | 8.95 |
| $(NH_4)_2S_2O_3$ | 24.80 |
| Thiamine | 0.01 |
| Glucose | 500.00 |
| Vitamin B12 | 0.01 |
| $NH_4OH$ 28% | Adjusted to pH 6.8 |

Subsequently, 2.5 L fermentors (Pierre Guerin) were filled with 600 or 620 mL of minimal medium (B2) and were inoculated to a biomass concentration of 3.2 $g \cdot L^{-1}$ with a preculture volume ranging between 80 to 100 mL.

Cell growth is controlled by phosphate, that is why the final phosphate concentration in batch medium B2 was adjusted to a value comprised between 0 to 20 mM, by addition of different concentrations of $KH_2PO_4$, $K_2HPO_4$ and $(NH_4)_2HPO_4$. In the same manner, the final phosphate concentration of F2 medium was adjusted to a value comprise between 5 to 30 mM, by addition of different concentrations of $KH_2PO_4$, $K_2HPO_4$ and $(NH_4)_2HPO_4$. Thiosulfate concentration in fedbatch medium can be adjusted in order to prevent a starvation of this compound during the culture.

TABLE 6

Culture batch mineral medium composition (B2)

| Compound | Concentration ($g \cdot L^{-1}$) |
|---|---|
| $Zn(CH_3COO)_2 \cdot 2H_2O$ | 0.0130 |
| $CuCl_2 \cdot 2H_2O$ | 0.0015 |
| $MnCl_2 \cdot 4H_2O$ | 0.0150 |
| $CoCl_2 \cdot 6H_2O$ | 0.0025 |
| $H_3BO_3$ | 0.0030 |
| $Na_2MoO_4 \cdot 2H_2O$ | 0.0025 |
| Fe(III) citrate $H_2O$ | 0.1064 |
| EDTA | 0.0084 |

TABLE 6-continued

| Culture batch mineral medium composition (B2) | |
|---|---|
| Compound | Concentration ($g \cdot L^{-1}$) |
| $MgSO_4 \cdot 7H_2O$ | 1.00 |
| $CaCl_2 \cdot 2H_2O$ | 0.08 |
| Citric acid | 1.70 |
| $(NH_4)_2S_2O_3$ | 7.74 |
| Thiamine | 0.01 |
| Vitamin B12 | 0.01 |
| Biotin | 0.10 |
| Glucose | 10 |
| $NH_4OH$ 28% | Adjusted to pH 6.8 |
| IPTG | 0.0047 |

TABLE 7

| Culture fedbatch medium composition (F2) | |
|---|---|
| Compound | Concentration ($g \cdot L^{-1}$) |
| $Zn(CH_3COO)_2 \cdot 2H_2O$ | 0.0104 |
| $CuCl_2 \cdot 2H_2O$ | 0.0012 |
| $MnCl_2 \cdot 4H_2O$ | 0.0120 |
| $CoCl_2 \cdot 6H_2O$ | 0.0020 |
| $H_3BO_3$ | 0.0024 |
| $Na_2MoO_4 \cdot 2H_2O$ | 0.0020 |
| Fe(III) citrate $H_2O$ | 0.0524 |
| EDTA | 0.0067 |
| $MgSO_4$ | 5.00 |
| $(NH_4)_2S_2O_3$ | 60.00 |
| Thiamine | 0.01 |
| Vitamin B12 | 0.01 |
| Biotin | 0.10 |
| Glucose | 500 |
| IPTG | 0.0047 |

The culture temperature was maintained constant at 37° C. and pH was maintained to the working value (6.8) by automatic addition of $NH_4OH$ solutions (10% and 28%). The initial agitation rate was set at 200 RPM during the batch phase and was increased up to 1000 RPM during the fedbatch phase. The initial airflow rate was set at 40 $NL \cdot h^{-1}$ during the batch phase and was augmented to 100 $NL \cdot h^{-1}$ at the beginning of the fedbatch phase. The dissolved oxygen concentration was maintained at values between 20 and 40%, preferentially 30% saturation by increasing the agitation.

IPTG was added in batch and fedbatch media when it was necessary at a final concentration of 20 μM. When it was needed, antibiotics were added at a concentration of 50 $mg \cdot L^{-1}$ for spectinomycin, 30 $mg \cdot L^{-1}$ for chloramphenicol and 100 $mg \cdot L^{-1}$ for ampicillin.

When the cell mass reached a concentration close to 5 $g \cdot L^{-1}$, the fedbatch was started with an initial flow rate of 5 $mL \cdot h^{-1}$. Feeding solution was injected with a sigmoid profile with an increasing flow rate that reached 24 $mL \cdot h^{-1}$ after 25 hours. The precise feeding conditions were calculated by the equation:

$$Q(t) = p1 + \frac{p2}{1 + e^{-p3(t-p4)}}.$$

where Q(t) is the feeding flow rate in $mL \cdot h^{-1}$ with p1=1.80, p2=22.4, p3=0.27, p4=6.50. This flow rate was increased from 10 to 50%, preferentially between 20 and 30% throughout the entire culture.

After 25 hours fedbatch, feeding solution pump was stopped and culture was finalized after glucose exhaustion.

Extracellular amino acids were quantified by HPLC after OPA/Fmoc derivatization and other relevant metabolites were analyzed using HPLC with refractometric detection (organic acids and glucose) and GC-MS after silylation.

Impact of combination of deletion of the metNIQ operon and/or overexpression of the ygaZH operon on methionine production was tested. The results are presented in Table 8 and Table 9.

TABLE 8

Maximal and final methionine yields produced in fedbatch cultures by the different strains. The performances of the strains of interest, strain 3, 1, and 6 are compared to the reference strain, strain 2 cultivated in the same conditions. The symbol ~ indicates that there is no difference between the strains, the symbol + indicates an increase between 1 to 3% and symbol ++ indicates an increase greater than 3%. For the definition of methionine/glucose yield see below.

| Strain | Strain 2 | Strain 3 | Strain 1 | Strain 6 |
|---|---|---|---|---|
| Number of repetitions | n = 8 | n = 1 | n = 7 | n = 3 |
| Max methionine yield % compared to the strain 2 | reference | ~ | + | ++ |
| Final methionine yield % compared to the strain 2 | reference | ~ | ++ | ++ |

The results presented on table 8 show that the deletion of metNIQ operon is of no benefit to the production of methionine (strain 3) in the genetic background of strain 2. Therefore, this genetic modification was tested in strain 4 with a different genetic background than strain 2. This assay shows a negative effect of the deletion of metNIQ operon on the methionine production (see table 9 below). Strains 4 and 5 were cultivated in 2 L reactors as described in patent application WO2013/001055.

TABLE 9

Maximal and final methionine yields produced in fedbatch cultures by the strain 5. The performances of the strain of interest (strain 5) are compared to the reference strain, strain 4 cultivated in the same conditions. The symbol − indicates a decrease greater than 4% compared to the reference strain. For the definition of methionine/glucose yield see below.

| Strain | Strain 4 | Strain 5 |
|---|---|---|
| Number of repetitions | n = 17 | n = 2 |
| Max methionine yield | reference | − |
| Final methionine yield | reference | − |

These results show that unlike prior art described for *C. glutamicum*, the deletion of metNIQ operon alone in *E. coli* does not enhance methionine production whatever the genetic background (strain 3 and 5). Moreover, performances of strain 5 are below performances of its mother strain (strain 4). Even if the overexpression of ygaZH leads to an increased production of methionine (strain 1, Table 8) at the end of the culture, surprisingly the combination of deletion of metNIQ operon and overexpression of ygaZH enhance the overall performances of methionine production from strain 6. This result was not expected since the deletion of metNIQ operon was shown as to be negative or neutral on the L-methionine production performances in different genetic backgrounds including the mother strain.

Determination of Methionine/Glucose Yield ($Y_{met}$)

The reactor volume was calculated by adding to the initial volume the amount of solutions added to regulate the pH and to feed the culture and by subtracting the volume used for sampling and lost by evaporation.

The fedbatch volume was followed continuously by weighing the feeding stock. The amount of injected glucose was then calculated on the basis of the injected weight, the density of the solution and the glucose concentration determined by the method of Brix ([Glucose]). The methionine yield was expressed as followed:

$$Y_{met} = \frac{Methionine_t * V_t - Methionine_0 * V_0 \times 100}{Consumed\ glucose_t}$$

With $Methionine_0$ and $Methionine_t$ respectively the initial and final methionine concentrations and $V_0$ and $V_t$ the initial and the instant t volumes.

The consumed glucose was calculated as follows:

$$fed\ volume_t = \frac{fed\ weight_0 - fed\ weight_t}{density\ fed\ solution}$$

Injected $Glucose_t$=fed $volume_t$*[Glucose]

Consumed $glucose_t$=$[Glucose]_0$*$V_0$+Injected Glucose−$[Glucose]_{residual}$*$V_t$ With $[Glucose]_0$, [Glucose], $[Glucose]_{residual}$ respectively the initial, the fed and the residual glucose concentrations.

Example 5

Combination of the Deletion of the L-Methionine Uptake System with the Overproduction of Different L-Methionine Secretion Systems from Various Microorganims in an *E. coli* Strain Overproducer of L-Methionine—Construction of Strains 7 to 15

The ygaZH homologous genes from *Citrobacter* species, *Raoultella* species, *Shigella* species, *Enterobacter* species, *Yersinia* species and *Photorhabdus* species were overexpressed in genetic background of strain 3.

Before using strain 3, the plasmid pME1089 was removed from this strain using a curing plasmid method as described by Heery et al, 1989 (according to Protocol 4). The cured cells without plasmid pME1089 but having retained the plasmid pME1109 were selected. The resulting strain was named strain 7.

Construction of Strains 8 to 15—Overproduction of Homologue L-Methionine Secretion Systems, Overexpression of ygaZH from Genus and Species Listed in Table 10.

To overexpress the ygaZH homologous genes listed in table 10, each couple of genes was cloned, as for ygaZH genes of *E. coli*, on the moderate copy number plasmid pCL1920 (Lerner & Inouye, 1990) with the use of the natural promoter and natural ribosome binding site of *E. coli* ygaZ gene. More precisely, ygaZH homologous genes were cloned into the pME1089 plasmid described above. As specified in table 11, the ygaZH homologous genes were either amplified from genomic DNA of the corresponding strain or chemically synthesized, with or without optimizing the codon usage to *E. coli* (as proposed by GeneArt® Gene Synthesis service with GeneOptimizer® software—Lifetechnologies). The amplified DNA fragments comprising the ygaZH homologous genes are disclosed in SEQ ID indicated in the Table 11. The resulting plasmids were named as mentioned in table 11. Finally each plasmid was transformed into strain 7, giving rise to strains 8 to 15 listed as "strain name" in table 11.

TABLE 10

YgaZH homologue proteins

| | YgaZ | | YgaH | |
|---|---|---|---|---|
| Organism | Acession Number | Name | Acession Number | Name |
| *Citrobacter koseri* | YP_001455539.1 NC_009792.1. ABV15103.1 | hypothetical protein CKO_04031 [*Citrobacter koseri* ATCC BAA-895] | YP_001455540.1 ABV15104.1 | hypothetical protein CKO_04032 [*Citrobacter koseri* ATCC BAA-895] |
| *Shigella flexneri* | WP_005122932.1 EIQ78635.1 | membrane protein [*Shigella flexneri*] | WP_005122930.1 EIQ78634.1 | branched-chain amino acid ABC transporter permease [*Shigella flexneri*] |
| *Raoultella ornithinolytica* | YP_007877063.1 AGJ89511.1 WP_015585890.1 | hypothetical protein RORB6_24155 [*Raoultella ornithinolytica* B6] | YP_007877062.1 AGJ89510.1 | L-valine exporter [*Raoultella ornithinolytica* B6] |
| *Enterobacter* sp. | YP_008107733.1 AGN85393.1 WP_020454909.1 | membrane protein [*Enterobacter* sp. R4-368] | YP_008107734.1 WP_020454910.1 AGN85394.1 | branched-chain amino acid ABC transporter permease [*Enterobacter* sp. R4-368] |
| *Yersinia enterocolitica* subsp. *Enterocolitica* | EKA28834.1 YWA314-01718 | putative amino acid transporter [*Yersinia enterocolitica* subsp. *enterocolitica* WA-314] | EKA288331 ou YWA314-01713 | hypothetical protein YE3239 [*Yersinia enterocolitica* subsp. *Enterocolitica* WA-314] |

TABLE 10-continued

YgaZH homologue proteins

| Organism | YgaZ Acession Number | YgaZ Name | YgaH Acession Number | YgaH Name |
|---|---|---|---|---|
| *Photorhabdus luminescens* subsp. *Laumondii* | NP_928590.1 CAE13573.1 | hypothetical protein plu1279 [*Photorhabdus luminescens* subsp. *laumondii* TTO1] | NP_928589.1 CAE13572.1 | hypothetical protein plu1278 [*Photorhabdus luminescens* subsp. *laumondii* TTO1] |
| *Citrobacter youngae* | WP_006687199.1 EFE06904.1 | membrane protein [*Citrobacter youngae*] putative azaleucine resistance protein AzlC [*Citrobacter youngae* ATCC 29220] | WP_006687198.1 EFE06903.1 | branched-chain amino acid ABC transporter permease [*Citrobacter youngae*] |
| *Citrobacter freundii* | WP_003839672.1 | hypothetical protein [*Citrobacter freundii*] | WP_003037297.1 | branched-chain amino acid ABC transporter permease [*Citrobacter freundii*] |

TABLE 11

Plasmids and strains carrying ygaZH homologue genes

| Microorganism | Chemical synthesis | Codon usage optimisation | SEQ ID N° | Plasmid name | Strain name |
|---|---|---|---|---|---|
| *Citrobacter koseri* | no | no | 23 | pME1277a | Strain 8 |
| *Shigella flexneri* | yes | no | 24 | pME1274a | Strain 9 |
| *Raoultella ornithinolytica* | yes | yes | 25 | pME1275a | Strain 10 |
| *Enterobacter* sp. | yes | yes | 26 | pME1283a | Strain 11 |
| *Yersinia enterocolitica* subsp. *Enterocolitica* | no | no | 27 | pME1287a | Strain 12 |
| *Photorhabdus luminescens* subsp. *Laumondii* | no | no | 28 | pME1281a | Strain 13 |
| *Citrobacter youngae* | yes | yes | 29 | pME1311a | Strain 14 |
| *Citrobacter freundii* | yes | yes | 30 | pME1307a | Strain 15 |

Example 6

Production of L-Methionine by Fermentation in Flask Experiments

Recombinant L-methionine producers having the deletion of metNIQ operon combined to the overexpression of different L-methionine secretion systems from various microorganisms (homologous to YgaZH from *E. coli*) were evaluated in small Erlenmeyer flasks.

A 5.5 mL preculture was grown at 30° C. for 21 hours in a mixed medium (10% LB medium (Sigma 25%) with 2.5 $g \cdot L^{-1}$ glucose and 90% minimal medium PC1, Table 12). It was used to inoculate a 50 mL culture to an $OD_{600}$ of 0.2 in medium PC1. Spectinomycin and kanamycin were added at a concentration of 50 $mg \cdot L^{-1}$, chloramphenicol at 30 $mg \cdot L^{-1}$ and gentamycin at 10 $mg \cdot L^{-1}$ when it was necessary. The temperature of the cultures was 37° C. When the culture had reached an $OD_{600}$ of 5 to 7, extracellular amino acids were quantified by HPLC after OPA/Fmoc derivatization and other relevant metabolites were analyzed using HPLC with refractometric detection (organic acids and glucose) and GC-MS after silylation.

TABLE 12

Minimal medium composition (PC1)

| Compound | Concentration ($g \cdot L^{-1}$) |
|---|---|
| $ZnSO_4 \cdot 7H_2O$ | 0.0040 |
| $CuCl_2 \cdot 2H_2O$ | 0.0020 |

TABLE 12-continued

Minimal medium composition (PC1)

| Compound | Concentration ($g \cdot L^{-1}$) |
|---|---|
| $MnSO_4 \cdot H_2O$ | 0.0200 |
| $CoCl_2 \cdot 6H_2O$ | 0.0080 |
| $H_3BO_3$ | 0.0010 |
| $Na_2MoO_4 \cdot 2H_2O$ | 0.0004 |
| $MgSO_4 \cdot 7H_2O$ | 1.00 |
| Citric acid | 6.00 |
| $CaCl_2 \cdot 2H_2O$ | 0.04 |
| $K_2HPO_4$ | 8.00 |
| $Na_2HPO_4$ | 2.00 |
| $(NH_4)_2HPO_4$ | 8.00 |
| $NH_4Cl$ | 0.13 |
| NaOH 4M | Adjusted to pH 6.8 |
| $FeSO_4 \cdot 7H_2O$ | 0.04 |
| Thiamine | 0.01 |
| Glucose | 20.00 |
| Ammonium thiosulfate | 5.61 |
| Vitamin B12 | 0.01 |
| MOPS | 20.00 |
| IPTG | 0.0048 |

TABLE 13

Methionine yield ($Y_{met}$) in g methionine/% g of glucose produced in flask culture by the strains of interest, carrying homologues of ygaZH genes and the deletion of metNIQ operon. For the precise definition of methionine/glucose yield see below. "n" indicates the number of repeats.

| Strain | $Y_{met}$ |
|---|---|
| Strain 3<br>Reference strain<br>n = 3 | 18.0 |
| Strain 6<br>n = 3 | 18.7 |
| Strain 8<br>n = 2 | 19.6 |
| Strain 9<br>n = 2 | 18.7 |
| Strain 10<br>n = 2 | 18.4 |
| Strain 11<br>n = 2 | 19.4 |
| Strain 12<br>n = 2 | 18.0 |
| Strain 13<br>n = 2 | 18.4 |
| Strain 14<br>n = 2 | 19.6 |
| Strain 15<br>n = 2 | 19.6 |

As can be seen in table 13, overexpression of ygaZH homologous genes from various microorganisms in the L-methionine producer carrying the deletion of metNIQ operon leads to equivalent or better performances than those obtained with strain 6 which overexpresses ygaZH from *E. coli*. The homologous L-methionine secretion systems from other microorganisms than *E. coli* can replace the endogenous proteins of the bacterium. The homologous proteins YgaZH from *Citrobacter Koseri* (strain 8, Ymet=19.6 g/g), *Citrobacter youngae* (strain 14, Ymet=19.6 g/g), *Citrobacter freundii* (strain 15, Ymet=19.6 g/g) and *Enterobacter* sp. (Strain 11, Ymet=19.4 g/g) showed the best L-methionine yields of production compared to strain 6 (Ymet=18.7 g/g).

The methionine yield was expressed as followed:

$$Y_{met} = \frac{\text{methionine (g)}}{\text{consummed glucose (g)}} * 100$$

REFERENCES

Anderson, 1946, *Proc. Natl. Acad. Sci. USA* 32:120-128.

Carrier T., Keasling J. D., 1999, *Biotechnology Progress*, 15:58-64

Datsenko K. A., Wanner B. L., 2000, *Proceedings of the National Academy of Sciences of the USA*, 97:6640-6645

Heery D. M., Powell R., Gannon F., Dunican L. K., 1989, *Nucleic Acids Res.* 17(23):10131

Jones P. M. and George A. M., 1999, *FEMS Microbiol. Lett.* 179:187-202

Kadner R. J. and Winkler H. H., 1975, *Journal of Bacteriology.* 123(3):985-991

Kadner R. J., 1974, *Journal of Bacteriology.* 117(1):232-241

Kadner R. J., 1975, *Journal of Bacteriology.* 122(1):110-119

Lerner C. G. and Inouye M., 1990, *Nucleic Acids Research*, 18(15):4631

Liebl et al., 1989, *Appl. Microbiol. Biotechnol.* 32: 205-210.

Merlin C., Gardiner G., Durand S., Masters M., 2002, *Journal of Bacteriology.* 184(19):5513-5517

Miller, 1992; *"A Short Course in Bacterial Genetics: A Laboratory Manual and Handbook for Escherichia coli and Related Bacteria"*, Cold Spring Harbor Laboratory Press, Cold Spring Harbor, N.Y.

Riedel et al., 2001, *J. Mol. Microbiol. Biotechnol.* 3: 573-583.

Saunderson C. L., 1985, *British Journal of Nutrition*, 54:621-633

Schaefer et al. 1999, *Anal. Biochem.* 270: 88-96.

Trötschel C., Deutenberg D., Bathe B., Burkovski A., Kramer R., 2005, *Journal of Bacteriology.* 187(11): 3786-3794

The invention claimed is:

1. A method for the fermentative production of methionine or its derivatives comprising:

a. culturing a recombinant *E. coli* wherein in said *E. coli*, at least one gene chosen among metN, metI or metQ is attenuated and the genes ygaZH are overexpressed, in an appropriate culture medium comprising a fermentable source of carbon and a source of sulphur, and b. recovering methionine and/or its derivatives from the culture medium;

wherein said ygaZH genes are coding for the YgaZ and YgaH proteins, respectively, wherein the YgaZ protein comprises the amino acid sequence of SEQ ID NOS: 1, 3, 5, 7, 9, 11, 13, 15, 17, or 19; and the YgaH protein comprises the amino acid sequence of SEQ ID NOS: 2, 4, 6, 8, 10, 12, 14, 16, 18, or 20; and wherein said recombinant *E. coli* strain overproduces methionine and/or its derivatives compared to an untransformed *E. coli* strain.

2. The method of claim 1, wherein the recombinant *E. coli* comprises:

a. deletion of at least one gene chosen among metN, metI or metQ, and b. overexpression of the genes ygaZH.

3. The method of claim 1, wherein said ygaZH genes are chosen among the group consisting in homologous genes from *Citrobacter* species, *Shigella* species, *Raoultella* species, *Enterobacter* species, *Yersinia* species and *Photorhabdus* species.

4. The method of claim 1, wherein said ygaZH homologous genes originate from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii.*

5. The method of claim 1, wherein growth of the recombinant *E. coli* is subjected to limitation or deficiency for one or several inorganic substrate(s) in the culture medium.

6. The method of claim 5, wherein said inorganic substrates comprise phosphate and/or potassium.

* * * * *